(12) United States Patent
Severns et al.

(10) Patent No.: US 6,184,188 B1
(45) Date of Patent: *Feb. 6, 2001

(54) FRAGRANCE DELIVERY SYSTEM FOR LIQUID DETERGENT COMPOSITIONS

(75) Inventors: John Cort Severns, West Chester; Mark Robert Sivik, Fairfield; Jill Bonham Costa, Cincinnati; Frederick Anthony Hartman, Cincinnati; Joseph Paul Morelli, Cincinnati, all of OH (US)

(73) Assignee: The Procter & Gamble Company, Cincinnati, OH (US)

( * ) Notice: Under 35 U.S.C. 154(b), the term of this patent shall be extended for 0 days.

This patent is subject to a terminal disclaimer.

(21) Appl. No.: 09/242,650

(22) PCT Filed: Aug. 19, 1997

(86) PCT No.: PCT/US97/14664

§ 371 Date: Mar. 18, 2000

§ 102(e) Date: Mar. 18, 2000

(87) PCT Pub. No.: WO98/07814

PCT Pub. Date: Feb. 26, 1998

Related U.S. Application Data

(60) Provisional application No. 60/024,117, filed on Aug. 19, 1996.

(51) Int. Cl.[7] ................................. C11D 3/20; C11D 3/50
(52) U.S. Cl. ..................... 510/101; 510/107; 510/337; 510/338; 510/505
(58) Field of Search ................................ 510/101, 107, 510/276, 337, 338, 505

(56) References Cited

U.S. PATENT DOCUMENTS

| | | | |
|---|---|---|---|
| 3,779,932 | 12/1973 | Jaggers et al. | 252/108 |
| 3,849,326 | 11/1974 | Jaggers et al. | 252/89 |
| 3,870,759 | 3/1975 | Inamoto et al. | 260/586 |
| 4,524,018 | 6/1985 | Yemoto et al. | 252/522 |
| 4,994,266 | 2/1991 | Wells | 424/76.7 |
| 5,081,111 | 1/1992 | Akmoto et al. | 525/285 |
| 5,232,612 | 8/1993 | Trinh et al. | 252/8.6 |
| 5,266,592 | 11/1993 | Grub et al. | 515/452 |
| 5,378,468 | 1/1995 | Suffis et al. | 424/401 |
| 5,506,201 | 4/1996 | McDermott et al. | 512/4 |
| 5,626,852 | 5/1997 | Suffis et al. | 424/401 |
| 5,739,100 | 4/1998 | Horino et al. | 512/25 |

FOREIGN PATENT DOCUMENTS

| | | | |
|---|---|---|---|
| 1923223 | 5/1969 | (DE) . | |
| 2509967 | 3/1975 | (DE) | C07C/69/02 |
| 0 786 247 | 7/1997 | (EP) | A61K/7/46 |
| 7-179328 | 7/1995 | (JP) | A61K/7/46 |
| WO 95/04809 | 2/1995 | (WO) | C11D/3/50 |
| WO 95/16660 | 6/1995 | (WO) | A61K/7/46 |
| WO 96/02625 | 2/1996 | (WO) | C11D/3/50 |
| WO 96/14827 | 5/1996 | (WO) | A61K/7/46 |

*Primary Examiner*—Kery Fries
(74) *Attorney, Agent, or Firm*—Richard S. Echler, Sr.; Kim W. Zerby; Steven W. Miller

(57) ABSTRACT

This invention is a fabric delivery system for liquid laundry detergent compositions which comprises a β-ketoester selected from a Markush group of β-ketoesters. Laundry compositions also contain surfactants and carriers.

17 Claims, No Drawings

FRAGRANCE DELIVERY SYSTEM FOR LIQUID DETERGENT COMPOSITIONS

CROSS REFERENCE

This application claims priority under Title 35, United States Code 119(e) from Provisional Application Serial No. 60/024,117, filed Aug. 19, 1996.

FIELD OF THE INVENTION

The present invention relates to liquid laundry detergent compositions useful for hand-washing fabric, comprising one or more β-ketoester pro-fragrance compounds which release fragrance raw material alcohols, ketones, and mixtures thereof, thereby providing a "freshness" or "clean" scent to fabric. The present invention also relates to a method for providing a fragrance benefit to laundered fabric by contacting soiled fabric with a laundry detergent composition described herein.

BACKGROUND OF THE INVENTION

In addition to the removal of stains, dirt, soil, grime, and grease from fabric, laundry detergent formulators have attempted to deliver a "fresh" or "clean" odor to washed clothing to provide an olfactory aesthetic benefit and to serve as a signal that the product is effective. Laundry detergent compositions, including rinse-added fabric softeners and dryer-added substrates, are currently formulated with perfume and fragrance ingredients which are aesthetically pleasing to the consumer and which attempt to deliver a prolonged "fragrance" or "pleasurable smell" to fabric which has been laundered via automatic appliance.

Liquid laundry detergent compositions are typically formulated with adjunct materials which are designed and formulated to work in high or low density liquid laundry detergent compositions. For example, certain enzymes, bleaches, soil release agents, and dispersants which comprise granular laundry detergent compositions may not be compatible with liquid laundry detergent formulations. Therefore, liquid laundry detergents comprise adjunct materials which are especially designed to fit the special needs of liquid compositions.

Attempts have been made to deliver perfume ingredients, especially fragrance raw material alcohols and ketones, which have an enduring fragrance benefit, from liquid laundry detergent compositions. The admixture of fragrance and perfume raw materials into a perfume component, which is subsequently added to the liquid laundry composition, may provide a short-term fragrance benefit, however, these materials have, in general, failed to provide a lasting fragrance benefit to fabric.

Accordingly, there remains a need in the art for a fragrance delivery system wherein fragrance raw materials are delivered to fabric by way of a liquid laundry detergent composition comprising one or more pro-fragrance or pro-accord compounds having high substantivity and water dispersing properties which provides the cleaned clothing or fabric with a "fresh" or "clean" smell for a protracted period after washing. The aforementioned laundry detergent compositions are typically granular detergents or laundry bars

BACKGROUND ART

The following relate to the subject matter of fragrance ingredients. U.S. Pat. No. 5,626,852 Suffis et al, issued May 6, 1997; U.S. Pat. No. 5,232,612 Trinh et al, issued Aug. 3, 1996; U.S. Pat. No. 5,506,201 McDermon et al., issued Apr. 9, 1996; U.S. Pat. No. 5,378,468 Suffis et al., issued Jan. 3, 1995; U.S. Pat. No. 5,266,592 Grub et al., issued Nov. 30, 1993; U.S. Pat. No. 5,081,111 Akimoto et al., issued Jan. 14, 1992; U.S. Pat. No. 4,994,266 Wells, issued Feb. 19, 1991; U.S. Pat. No. 4,524,018 Yemoto et al., issued Jun. 18, 1985; U.S. Pat. No. 3,849,326 Jaggers et al, issued Nov. 19, 1974; U.S. Pat. No. 3,779,932 Jaggers et al., issued Dec. 18, 1973; JP 07-179,328 published Jul. 18, 1995; JP 05-230496 published Sep. 7, 1993; WO 96/14827 published May 23, 1996; WO 95/04,809 published Feb. 16, 1995; and WO 95/16660 published Jun. 22, 1995. In addition, P. M. Muller, D. Lamparsky Perfumes Art. Science. & Technology Blackie Academic & Professional, (New York, 1994) is included herein by reference.

SUMMARY OF THE INVENTION

The present invention meets the aforementioned needs in that it has been surprisingly discovered that fragrance raw materials can be delivered onto fabric "through the wash" by way of a fragrance delivery system comprised of single precursor pro-fragrance or pro-accord compounds having high fabric substantivity and that these compounds release fragrance raw materials thereby imparting a "fresh" or "clean" aesthetic odor benefit to the fabric. In addition to the short-term pleasurable odor benefits, the profragrances or pro-accords according to the present invention continue to release their fragrance raw materials for as long as several weeks depending upon the structure of the pro-fragrance.

The pro-fragrances and pro-accords described herein comprise fragrance raw material alcohols in a stable, releasable β-ketoester form. The pro-fragrance containing liquid laundry detergent compositions of the present invention can comprise any number of profragrances which when taken together are capable of releasing complex perfume fragrances. However, the β-ketoesters of the present invention which are pro-accords are capable of undergoing chemical transformation and thereby releasing one or more fragrance raw materials in addition to the fragrance raw material alcohol used to prepare the original parent pro-accord. In addition, the pro-fragrances and pro-accords of the present invention are suitable for delivery of any type of fragrance "characteristic" desired by the formulator.

The first aspect of the present invention relates to a liquid laundry detergent composition which provides fabric with enhanced fragrance longevity, comprising:

a) at least about 0.01%, preferably from about 0.01% to about 15%, more preferably from about 1% to about 5%, most preferably from about 0.1% to about 1% by weight, of a β-ketoester having the formula:

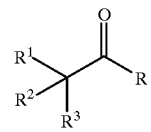

wherein R is alkoxy derived from a fr-agrance raw material alcohol; $R^1$, $R^2$ and $R^3$ are each independently hydrogen, $C_1$–$C_{30}$ substituted or unsubstituted linear alkyl, $C_3$–$C_{30}$ substituted or unsubstituted branched alkyl, $C_3$–$C_{30}$ substituted or unsubstituted cyclic alkyl, $C_2$–$C_{30}$ substituted or unsubstituted linear alkenyl, $C_3$–$C_{30}$ substituted or unsubstituted branched alkenyl, $C_3$–$C_{30}$ substituted or unsubstituted cyclic alkenyl, $C_2$–$C_{30}$ substituted or unsubstituted linear alkynyl, $C_3$–$C_{30}$ substituted or unsubstituted branched alkynyl, $C_6$–$C_{30}$ substituted or unsubstituted aryl, $C_2$–$C_{20}$ substituted or unsubstituted alkyleneoxy, $C_3$–$C_{20}$ substituted or unsubstituted alkyleneoxyalkyl, $C_7$–$C_{20}$ substituted or unsubstituted alkylenearyl, $C_6$–$C_{20}$ substituted or unsubstituted alkyleneoxyaryl, and mixtures thereof; provided at least one $R^1$, $R^2$, or $R^3$ is a unit having the formula:

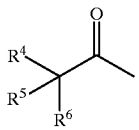

wherein $R^4$, $R^5$, and $R^6$ are each independently hydrogen, $C_1$–$C_{30}$ substituted or unsubstituted linear alkyl, $C_3$–$C_{30}$ substituted or unsubstituted branched alkyl, $C_3$–$C_{30}$ substituted or unsubstituted cyclic alkyl, $C_1$–$C_{30}$ substituted or unsubstituted linear alkoxy, $C_3$–$C_{30}$ substituted or unsubstituted branched alkoxy, $C_3$–$C_{30}$ substituted or unsubstituted cyclic alkoxy, $C_2$–$C_{30}$ substituted or unsubstituted linear alkenyl, $C_3$–$C_{30}$ substituted or unsubstituted branched alkenyl, $C_3$–$C_{30}$ substituted or unsubstituted cyclic alkenyl, $C_2$–$C_{30}$ substituted or unsubstituted linear alkynyl, $C_3$–$C_{30}$ substituted or unsubstituted branched alkynyl, $C_6$–$C_{30}$ substituted or unsubstituted alkylenearyl, $C_6$–$C_{30}$ substituted or unsubstituted aryl; or $R^4$, $R^5$, and $R^6$ can be taken together to form $C_6$–$C_{30}$ substituted or unsubstituted aryl; and mixtures thereof;

b) at least about 0.01% by weight, preferably from about 0.1% to about 60%, more preferably from about 0.1% to about 30% by weight, of a detersive surfactant selected from the group consisting of anionic, cationic, nonionic, zwitterionic, ampholytic surfactants, and mixtures thereof, preferably said surfactant is an anionic surfactant;

c) the balance carriers and adjunct ingredients, said adjunct ingredients are selected from the group consisting of builders, optical brighteners, bleaches, bleach boosters, bleach catalysts, bleach activators, soil release polymers, dye transfer agents, dispersents, enzymes, suds suppressers, dyes, perfiunes, colorants, filler salts, hydrotropes, enzymes, photoactivators, fluorescers, fabric conditioners, hydrolyzable surfactants, preservatives, anti-oxidants, chelants, stabilizers, anti-shrinkage agents, anti-wrinkle agents, germicides, fungicides, anti corrosion agents, and mixtures thereof;

wherein said laundry composition has a pH of from about 7.2 to about 8.9 when measured as a 10% solution in water.

A further aspect of the present invention relates to methods for providing an extended "fresh" and "clean" odor benefit to fabric comprising the step of laundering fabric in an aqueous solution of a liquid laundry detergent composition comprising one or more ,-ketoester pro-fragrances described herein.

A yet fuirther aspect of the present invention relates to non-aqueous liquid detergent compositions. These and other objects, features and advantages will become apparent to those of ordinary skill in the art from a reading of the following detailed description and the appended claims.

All percentages, ratios and proportions herein are by weight, unless otherwise specified. All temperatures are in degrees Celsius (°C) unless otherwise specified. All documents cited are in relevant part, incorporated herein by reference.

DETAILED DESCRIPTION OF THE INVENTION

The present invention comprises liquid laundry detergent compositions having a fragrance delivery system which comprises one or more β-ketoester pro-fragrances or pro-accords suitable for use in providing an extended fragrance benefit to fabric. The liquid laundry detergent compositions may optionally comprise bleaching materials or the compositions may be non-aqueous liquid detergents. The present invention thus comprises the following preferred formulations.

Preferred liquid laundry detergent compositions of the present invention comprise:

a) at least about 0.01%, preferably from about 0.01% to about 15%, more preferably from about 1% to about 5%, most preferably from about 0.1% to about 1% by weight, of a β-ketoester pro-fragrance described herein below;

b) at least about 0.01% by weight, preferably from about 0.1% to about 60%, more preferably from about 0.1% to about 30% by weight, of a detersive surfactant selected from the group consisting of anionic, cationic, nonionic, zwitterionic, ampholytic surfactants, and mixtures thereof, preferably said surfactant is an anionic surfactant;

c) at least about 0.001% by weight, of a protease enzyme selected from the group consisting of Protease A, Protease B, Protease D, subtilisin 309 variants, and mixtures thereof, and d) the balance carriers and adjunct ingredients, said adjunct ingredients are selected from the group consisting of builders, optical brighteners, bleaches, bleach boosters, bleach catalysts, bleach activators, soil release polymers, dye transfer agents, dispersents, enzymes, suds suppressers, dyes, perfuimes, colorants, filler salts, hydrotropes, enzymes, photoactivators, fluorescers, fabric conditioners, hydrolyzable surfactants, preservatives, anti-oxidants, chelants, stabilizers, anti-shrinkage agents, anti-wrinkle agents, germicides, fingicides, anti corrosion agents, and mixtures thereof.

wherein said laundry composition has a pH of from about 7.2 to about 8.9 when measured as a 10% solution in water.

A further preferred liquid laundry detergent composition according to the present invention comprises:

a) at least about 0.01%, preferably from about 0.01% to about 15%, more preferably from about 1% to about 5%, most preferably from about 0.1% to about 1% by weight, of a β-ketoester pro-fragrance described herein below;

b) at least about 0.01% by weight, preferably from about 0.1% to about 60%, more preferably from about 0.1% to about 30% by weight, of an anionic detersive surfactant;

c) at least about 0.01% by weight, preferably from about 0.1% to about 60%, more preferably from about 0.1% to about 30% by weight, of a nonionic detersive surfactant;

d) at least about 0.001% by weight, of a protease enzyme selected from the group consisting of Protease A, Protease B, Protease D, subtilisin 309 variants, and mixtures thereof, and e) the balance carriers and adjunct ingredients, said adjunct ingredients are selected from the group consisting of builders, optical brighteners, bleaches, bleach boosters, bleach catalysts, bleach activators, soil release polymers, dye transfer agents, dispersents, enzymes, suds suppressers, dyes, perfuimes, colorants, filler salts, hydrotropes, enzymes, photoactivators, fluorescers, fabric conditioners, hydrolyzable surfactants, preservatives, anti-oxidants, chelants, stabilizers, anti-shrinkage agents, anti-wrinkle agents, gennicides, fungicides, anti corrosion agents, and mixtures thereof.

wherein said laundry composition has a pH of from about 7.2 to about 8.9 when measured as a 10% solution in water.

Another preferred liquid laundry detergent composition according to the present invention comprises:

a) at least about 0.01%, preferably from about 0.01% to about 15%, more preferably from about 1% to about 5%, most preferably from about 0.1% to about 1% by weight, of a β-ketoester pro-fragrance described herein below;

b) at least about 0.01%, preferably from about 0.1% to about 60%, more preferably from about 0.1% to about 30% by weight, of an anionic detersive surfactant selected from the group consisting of alkyl sulfates, alkyl ethoxy sulfates, and mixtures thereof;

c) at least about 0.01%, preferably from about 0.1% to about 60%, more preferably from about 0.1% to about 30% by weight, of a nonionic detersive surfactant;

d) at least about 0.001% by weight, of a protease enzyme selected from the group consisting of Protease A, Protease B, Protease D, subtilisin 309 variants, and mixtures thereof;

e) at least about 0.1% by weight preferably from about 0.1% to about 10%, more preferably from about 0.5% to about 5% by weight, of a modified or unmodified polyalkyleneimine dispersant;

f) optionally at least about 0.1%, by weight of a bleach; and g) the balance carriers and adjunct ingredients, said adjunct ingredients are selected from the group consisting of builders, optical brighteners, bleach boosters, bleach catalysts, bleach activators, soil release polymers, dye transfer agents, enzymes, suds suppressers, dyes, perfimnes, colorants, filler salts, hydrotropes, enzymes, photoactivators, fluorescers, fabric conditioners, hydrolyzable surfactants, preservatives, anti-oxidants, chelants, stabilizers, anti-shrinkage agents, anti-wrinkle agents, germicides, fimgicides, anti corrosion agents, and mixtures thereof.

wherein said laundry composition has a pH of from about 7.2 to about 8.9 when measured as a 10% solution in water.

A preferred non-aqueous liquid detergent composition according to the present invention comprises:

a) from about 49% to about 99.95%, preferably from about 55% to about 98.9% by weight, a structured, surfactant-containing liquid phase, said phase formed by combining:
  i) from about 1% to about 80% by weight of said liquid phase, one or more non-aqueous organic diluents; and
  ii) from about 20% to about 99% by weight of said liquid phase, a surfactant selected from the group consisting of anionic, nonionic, cationic surfactants, and mixtures thereof;

b) at least about 0.01%, preferably from about 0.01% to about 15%, more preferably from about 1% to about 5%, most preferably from about 0.1% to about 1% by weight, of a β-ketoester pro-fragrance described herein below; and c) the balance adjunct ingredients which are substantially insoluble in said liquid phase, said adjuncts comprising particulate material having a size from about 0.1 micron to about 1500 microns, wherein said ingredients are preferably selected from the group consisting of peroxygen bleaching agents, bleach activators, organic detergent builders, sources of alkalinity, and mixtures thereof.

The preferred liquid laundry detergent compositions of the present invention comprise certain anionic and nonionic surfactants, enzymes, and dispersing agents that when used in combination with the β-ketoester pro-fragrances of the present invention, provides improved cleaning and freshness benefits for all fabric. The liquid laundry detergent compositions of the present invention comprise the following ingredients.

The β-ketoester pro-accords of the present invention are also useful in liquid dishwashing detergents, which in their basic form comprise:

a) at least about 0.01%, preferably from about 0.01% to about 15%, more preferably from about 1% to about 5%, most preferably from about 0.1% to about 1% by weight, of a β-ketoester as described herein;

b) at least about 0.01% by weight, preferably from about 0.1% to about 60%, more preferably from about 0.1% to about 30% by weight, of an anionic detersive surfactant;

c) at least about 0.01% by weight, preferably from about 0.1% to about 60%, more preferably from about 0.1% to about 30% by weight, of a nonionic detersive surfactant;

d) the balance carriers and adjunct ingredients, said carriers preferably water.

Fragrance Delivery System

The laundry detergent compositions of the present invention comprise a fragrance delivery system which lays down one or more "pro-fragrance" compounds onto the fabric surface during the laundry wash cycle which are capable of releasing a fragrance raw material alcohol or in the case of "pro-accords" the compounds are capable of releasing a mixture of fragrance raw materials. The key advantages provided by the β-ketoester pro-fragrances or pro-accords of the present invention include chemical stability in the final product matrix, ease of formulation into the product matrix, and a highly desirable rate of fragrance raw material alcohol release.

The β-ketoester profragrances and pro-accords of the present invention begin delivering the fragrance raw materials to the fabric surface once the fabric is exposed to the laundry liquor. For the purposes of the present invention the term "pro-fragrance" is defined as "a β-ketoester which releases a fragrance raw material alcohol" whereas a "pro-accord" is defined as "β-ketoester which release two or more fragrance raw materials". For the purposes of the present invention, however, since a material that is a "pro-fragrance" in one embodiment can serve as a "pro-accord" in a different embodiment, the term "pro-fragrance" is used interchangeably with the term "pro-accord" and either term may be used to stand equally well for either β-ketoester pro-fragrance molecules, β-ketoester pro-accord molecules, or both collectively. These "pro-fragrance" compounds are rapidly deposited onto the fabric surface due to the high fabric substantivity of the compounds and once deposited, begin to release the fragrance raw material alcohols during the wash and drying cycles. Because the β-ketoester "pro-fragrances" of the present invention generally have a higher molecular weight than uncombined fragrance raw material alcohols are therefore less volatile, the "pro-fragrances" of the present invention are a means for effectively delivering fragrance raw materials to the fabric surface even upon exposure to prolonged heating which occurs during automatic dryer usage. Once the laundry cycle is complete, that is the clothing or fabric is dry and ready for use, the "pro-fragrance" continues to release the fragrance raw material alcohol and because this release of material is protracted, the fabric remains "fresh" and "clean" smelling longer.

For the purposes of the present invention "fragrance raw materials" are herein defined as alcohols and ketones having a molecular weight of at least about 100 g/mol and which are useful in imparting an odor, fragrance, essence, or scent either alone or in combination with other "fragrance raw material alcohols and ketones".

Most of the fragrance raw material alcohols which comprise the β-ketoester "pro-fragrances" of the present invention are not deliverable as individual compounds to fabric via the laundry cycle either due to solubility factors (not sufficiently soluble in the liquid laundry liquor), substantivity factors (do not sufficiently adhere to fabric surface), or volatility factors (evaporation during storage). Therefore, the profragrances described herein are a means for delivering certain fragrance raw materials to fabric which could not have previously been effectively or efficiently delivered.

β-Ketoester Pro-frances

The compositions according to the present invention comprise one or more β-ketoesters having the formula:

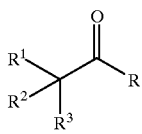

wherein R is alkoxy derived from a fragrance raw material alcohol. Non-limiting examples of preferred fragrance raw material alcohols include 2,4-dimethyl-3-cyclohexene-1-methanol (Floralol), 2,4-dimethyl cyclohexane methanol (Dihydro floralol), 5,6dimethyl-1-methylethenylbicyclo[2.2.1]hept-5-ene-2-methanol (Arbozol), α,α,-4-trimethyl-3-cyclohexen-1-methanol (α-terpineol), 2,4,6-trimethyl-3-cyclohexene-1-methanol (Isocyclo geraniol), 4-(1-methylethyl)cyclohexane methanol (Mayol), α-3,3-trimethyl-2-norborane methanol, 1,1-dimethyl-1-(4-methylcyclohex-3-enyl)methanol, 2-phenylethanol, 2-cyclohexyl ethanol, 2-(o-methylphenyl)-ethanol, 2-(m-methylphenyl)ethanol, 2-(p-methylphenyl)ethanol, 6,6-dimethylbicyclo-[3.1.1]hept-2-ene-2-ethanol (nopol), 2-(4-methylphenoxy)-ethanol, 3,3dimethyl-Δ²-β-norbornane ethanol (patchomint), 2-methyl-2-cyclohexylethanol, 1-(4-isopropylcyclohexyl)ethanol, 1-phenylethanol, 1,1-dimethyl-2-phenylethanol, 1,1-dimethyl-2-(4-methyl-phenyl)ethanol, 1-phenylpropanol, 3-phenylpropanol, 2-phenylpropanol (Hydrotropic Alcohol), 2-(cyclododecyl) propan-1-ol (Hydroxy-ambran), 2,2-dimethyl-3-(3-methylphenyl) propan-1-ol (Majantol), 2-methyl-3-phenylpropanol, 3-phenyl-2-propen-1-ol (cinnamyl alcohol), 2-methyl-3-phenyl-2-propen-1-ol (methylcinnamyl alcohol), α-n-pentyl-3-phenyl-2-propen-1-ol (α-amyl-cinnamyl alcohol), ethyl-3-hydroxy-3-phenyl propionate, 2-(4-methylphenyl)-2-propanol, 3-(4-methylcyclohex-3-ene)butanol, 2-methyl-4-(2,2,3-trimethyl-3-cyclopenten-1-yl)butanol, 2-ethyl4-(2,2,3-trimethyl-cyclopent-3-enyl)-2-buten-1-ol, 3-methyl-2-buten-1-ol (prenol), 2-methyl4-(2,2,3-trimethyl-3-cyclopenten-1-yl)-2-buten-1-ol, ethyl 3-hydroxybutyrate, 4-phenyl-3-buten-2-ol, 2-methyl4-phenylbutan-2-ol, 4-(4-hydroxyphenyl)butan-2-one, 4-(4-hydroxy-3-methoxyphenyl)-butan-2-one, 3-methyl-pentanol, 3-methyl-3-penten-1-ol, 1-(2-propenyl)cyclopentan-1-ol (plinol), 2-methyl4-phenylpentanol (Pamplefleur), 3-methyl-5-phenylpentanol (Phenoxanol), 2-methyl-5-phenylpentanol, 2-methyl-5-(2,3-dimethyltricyclo[2.2.1.0$^{(2,6)}$]hept-3-yl)-2-penten-1-ol (santalol), 4-methyl-1-phenyl-2-pentanol, 5-(2,2,3-tnimethyl-3-cyclopentenyl)-3-methylpentan-2-ol (sandalore), (1-methyl-bicyclo[2.1.1]hepten-2-yl)2-methylpent-1-en-3-ol, 3-methyl-1-phenylpentan-3-ol, 1,2dimethyl-3-(1-methylethenyl)cyclopentan-1-ol, 2-isopropyl-5-methyl-2-hexenol, cis-3-hexen-1-ol, trans-2-hexen-1-ol, 2-isoproenyl4-methyl4-hexen-1-ol (Lavandulol), 2-ethyl-2-prenyl-3-hexenol, 1-hydroxymethyl-4-iso-propenyl-1-cyclohexene (Dihydrocuminyl alcohol), 1-methyl-4-isopropenylcyclohex-6-en-2-ol (carvenol), 6-methyl-3-isopropenylcyclohexan-1-ol (dihydrocarveol), 1-methyl-4-iso-propenylcyclohexan-3-ol, 4-isopropyl-1-methylcyclohexan-3-ol, 4-tert-butylcyclo-hexanol, 2-tert-butylcyclohexanol, 2-tert-butyl-4-methylcyclohexanol (rootanol), 4-isopropyl-cyclohexanol, 4methyl-l-(1-methylethyl)-3-cyclohexen-1-ol, 2-(5,6,6-trimethyl-2-norbornyl)cyclohexanol, isobornylcyclohexanol, 3,3,5-trimethylcyclohexanol, 1-methyl-4-isopropylcyclohexan-3-ol, 1-methyl-4-isopropylcyclohexan-8-ol (dihydroterpineol), 1,2-dimethyl-3-(1-methylethyl) cyclohexan-1-ol, heptanol, 2,4-dimethylheptan-1-ol, 6-heptyl-5-hepten-2-ol (isolinalool), 2,4-dimethyl-2,6-heptandienol, 6,6-dimethyl-2-oxymethyl-bicyclo[3.1.1]hept-2-ene (myrtenol), 4-methyl-2,4-heptadien-1-ol, 3,4,5,6,6-pentamethyl-2-heptanol, 3,6-dimethyl-3-vinyl-5-hepten-2-ol, 6,6-dimethyl-3-hydroxy-2-methylenebicyclo[3.1.1]heptane, 1,7,7-timethylbicyclo[2.2.1]heptan-2-ol, 2,6-dimethylheptan-2-ol (dimetol), 2,6,6-timethylbicyclo[1.3.3]heptan-2-ol, octanol, 2-octenol, 2-methyloctan-2-ol, 2-methyl-6-methylene-7-octen-2-ol (myrcenol), 7-methyloctan-1-ol, 3,7-dimethyl-6-octenol, 3,7-dimethyl-7-octenol, 3,7-dimethyl-6-octen-1-ol (citronellol), 3,7-dimethyl-2,6-octadien-1-ol (geraniol), 3,7-dimethyl-2,6octadien-1-ol (nerol), 3,7-dimethyl-7-methoxyoctan-2-ol (osyrol), 3,7-dimethyl-l,6-octadien-3-ol (linalool), 3,7-dimethyloctan-1-ol (pelargol), 3,7-dimethyloctan-3-ol (tetrahydrolinalool), 2,4-octadien-1-ol, 3,7-dimethyl-6-octen-3-ol (dihydrolinalool), 2,6-dimethyl-7-octen-2-ol (dihydromyrcenol), 2,6-dimethyl-5,7-octadien-2-ol, 4,7-dimethyl4vinyl-6-octen-3-ol, 3-methyloctan-3-ol, 2,6-dimethyloctan-2-ol, 2,6-dimethyloctan-3-ol, 3,6-dimethyloctan-3-ol, 2,6-dimethyl-7-octen-2-ol, 2,6-dimethyl-3,5-octadien-2-ol (muguol), 3-methyl-1-octen-3-ol, 7-hydroxy-3,7-dimethyloctanal, 3-nonanol, 2,6-nonadien-1-ol, cis-6-nonen-1-ol, 6,8-dimethylnonan-2-ol, 3-(hydroxymethyl)-2-nonanone, 2-nonen-1-ol, 2,4-nonadien-1-ol, 3,7-dimethyl-1,6nonadien-3-ol, decanol, 9-decenol, 2-benzyl-M-dioxa-5-ol, 2-decen-1-ol, 2,4-decadien-1-ol, 4-methyl-3-decen-5-ol, 3,7,9-trimethyl- 1,6-decadien-3-ol (isobutyl linalool), undecanol, 2-undecen-1-ol, 10-undecen-1-ol, 2-dodecen-1-ol, 2,4-dodecadien-1-ol, 2,7,11-trimethyl-2,6,10-dodecatrien-1-ol (farnesol), 3,7,11-trimethyl- 1,6,10,-dodecatrien-3-ol (nerolidol), 3,7,11,15- tetramethylhexadec-2-en-1-ol (phytol), 3,7,11,15-tetramethylhexadec-1-en-3-ol (iso phytol), benzyl alcohol, p-methoxy benzyl alcohol (anisyl alcohol), para-cymen-7-ol (cuminyl alcohol), 4-methyl benzyl alcohol, 3,4-methylenedioxy benzyl alcohol, methyl salicylate, benzyl salicylate, cis-3-hexenyl salicylate, n-pentyl salicylate, 2-phenylethyl salicylate, n-hexyl salicylate, 2-methyl-5-isopropylphenol, 4-ethyl-2-methoxyphenol, 4-allyl-2-methoxyphenol (eugenol), 2-methoxy-4-(1-propenyl)phenol (isoeugenol), 4-allyl-2,6-dimethoxy-phenol, 4-tert-butylphenol, 2-ethoxy4-methylphenol, 2-methyl-4-vinylphenol, 2-isopropyl-5-methylphenol (thymol), pentyl-ortho-hydroxy benzoate, ethyl 2-hydroxy-benzoate, methyl 2,4-dihydroxy-3,6-dimethylbenzoate, 3-hydroxy-5-methoxy- 1-methylbenzene, 2-tert-butyl-4-methyl-1-hydroxybenzene, 1-ethoxy-2-hydroxy4-propenylbenzene, 4-hydroxytoluene, 4-hydroxy-3-methoxybenzaldehyde, 2-ethoxy-4-hydroxybenzaldehyde, decahydro-2-naphthol, 2,5,5-trimethyl-octahydro-2-naphthol, 1,3,3-trimethyl-2-norbomanol (fenchol), 3a,4,5,6,7,7a-hexahydro-2,4-dimethyl4,7-methano-1H-inden-5-ol, 3a,4,5,6,7,7a-hexahydro-3,4-dimethyl4,7-methano-1H-inden-5-ol, 2-methyl-2-vinyl-5-(1-hydroxy-1-methylethyl)tetrahydrofiian, β-caryophyllene alcohol, vanillin, ethyl vanillin, and mixtures thereof.

More preferably, the fragrance raw material alcohol is selected from the group consisting of cis-3-hexen-1-ol, hawthanol [admixture of 2-(o-methylphenyl)-ethanol, 2-(m-methylphenyl)ethanol, and 2-(p-methylphenyl)ethanol], heptan-1-ol, decan-1-ol, 2,4-dimethyl cyclohexane methanol, 4-methylbutan-1-ol, 2,4,6-trimethyl-3-cyclohexene-1-methanol, 4-(1-methylethylicyclohexane methanol, 3-(hydroxy-methyl)-2-nonanone, octan-1-ol, 3-phenylpropanol, Rhodinol 70 [3,7-dimethyl-7-octenol, 3,7-dimethyl-6-octenol admixture], 9-decen-1-ol, α-3,3-trimethyl-2-norborane methanol, 3-cyclohexylpropan-1-ol, 4-methyl-1-phenyl-2-pentanol, 3,6-dimethyl-3-vinyl-5-hepten-2-ol, phenyl ethyl methanol; propyl benzyl methanol, 1-methyl4-isopropenylcyclohexan-3-ol, 4-isopropyl- 1 -methylcyclohexan-3-ol (menthol), 4-tert-butylcyclohexanol, 2-tert-butyl-4-methylcyclohexanol, 4-isopropylcyclo-hexanol, trans-decahydro-β-naphthol, 2-tert-butylcyclohexanol, 3-phenyl-2-propen-1-ol, 2,7,11-trimethyl-2,6,10-dodecatrien-1-ol, 3,7-dimethyl-2,6-octadien-1-ol (geraniol), 3,7-dimethyl-2,6-octadien-1-ol (nerol), 4-methoxybenzyl alcohol, benzyl alcohol, 4-allyl-2-methoxyphenol, 2-methoxy4-(1-propenyl)phenol, vanillin, and mixtures thereof.

$R^1$, $R^2$, and $R^3$ are each independently hydrogen, $C_1$–$C_{30}$ substituted or unsubstituted linear alkyl, $C_3$–$C_{30}$ substituted or unsubstituted branched alkyl, $C_3$–$C_{30}$ substituted or unsubstituted cyclic alkyl, $C_2$–$C_{30}$ substituted or unsubstituted linear alkenyl, $C_3$–$C_{30}$ substituted or unsubstituted branched alkenyl, $C_3$–$C_{30}$ substituted or unsubstituted cyclic alkenyl, $C_2$–$C_{30}$ substituted or unsubstituted linear alkynyl, $C_3$–$C_{30}$ substituted or unsubstituted branched alkynyl, $C_6$–$C_{30}$ substituted or unsubstituted aryl, $C_2$–$C_{20}$ substituted or unsubstituted alkyleneoxy, $C_3$–$C_{20}$ substituted or unsubstituted alkyleneoxyalkyl, $C_7$–$C_{20}$ substituted or unsubstituted alkylenearyl, $C_6$–$C_{20}$ substituted or unsubstituted alkyleneoxyaryl, and mixtures thereof; provided at least one $R^1$, $R^2$, or $R^3$ is a unit having the formula:

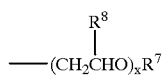

wherein $R^4$, $R^5$, and $R^6$ are each independently hydrogen, $C_1$–$C_{30}$ substituted or unsubstituted linear alkyl, $C_3$–$C_{30}$ substituted or unsubstituted branched alkyl, $C_3$–$C_{30}$ substituted or unsubstituted cyclic alkyl, $C_1$–$C_{30}$ substituted or unsubstituted linear alkoxy, $C_3$–$C_{30}$ substituted or unsubstituted branched alkoxy, $C_3$–$C_{30}$ substituted or unsubstituted cyclic alkoxy, $C_2$–$C_{30}$ substituted or unsubstituted linear alkenyl, $C_3$–$C_{30}$ substituted or unsubstituted branched alkenyl, $C_3$–$C_{30}$ substituted or unsubstituted cyclic alkenyl, $C_2$–$C_{30}$ substituted or unsubstituted linear alkynyl, $C_3$–$C_{30}$ substituted or unsubstituted branched alkynyl, $C_6$–$C_{30}$ substituted or unsubstituted alkylenearyl, $C_6$–$C_{30}$ substituted or unsubstituted aryl; or $R^4$, $R^5$, and $R^6$ can be taken together to form $C_6$–$C_{30}$ substituted or unsubstituted aryl; and mixtures thereof In one preferred embodiment at least two $R^2$, or $R^3$ units are hydrogen and $R^4$, $R^5$, and $R^6$ units are each hydrogen. In another preferred embodiment two $R^4$, $R^5$, and $R^6$ units are hydrogen and the remaining unit is $C_1$–$C_{20}$ substituted or unsubstituted linear alkyl, $C_3$–$C_{20}$ substituted or unsubstituted branched alkyl, $C_3$–$C_{20}$ substituted or unsubstituted cyclic alkyl; more preferably hexyl, heptyl, octyl, nonanyl, ω-hexenyl, ω-heptenyl, ω-octenyl, ω-nonenyl, and mixtures thereof. Also preferably $R^4$, $R^5$, and $R^6$ are taken together to form a $C_6$–$C_{30}$ substituted or unsubstituted aryl unit, preferably substituted or unsubstituted phenyl and naphthyl. Also preferred embodiments include providing $R^2$ and $R^3$ moieties which provide increased fabric substantivity or which facilitate the rate at which fragrance raw materials are released.

For the purposes of the present invention the term "substituted" as it applies to linear alkyl, branched alkyl, cyclic alkyl, linear alkenyl, branched alkenyl, cyclic alkenyl, branched alkoxy, cyclic alkoxy, alkynyl, and branched alkynyl units are defined as "carbon chains which comprise substitutents other than branching of the carbon atom chain", for example, other than the branching of alkyl units (e.g. isopropyl, isobutyl). Non-limiting examples of "substituents" include hydroxy, $C_1$–$C_{12}$ alkoxy, preferably methoxy; $C_3$–$C_{12}$ branched alkoxy, preferably isopropoxy; $C_3$–$C_{12}$ cyclic alkoxy; nitrilo; halogen, preferably chloro and bromo, more preferably chloro; nitro; morpholino; cyano; carboxyl, non-limiting examples of which are —CHO; —$CO_2^-M^+$, —$CO_2R^9$; —$CONH_2$; —$CONHR^9$; —$CONR^9_2$; wherein $R^9$ is $C_1$–$C_{12}$ linear or branched alkyl); —$SO_3^-M^+$; —$OSO_3^-M^+$; —$N(R^{10})_2$; and —$N^+(R^{10})_3X^-$ wherein each $R^{10}$ is independently hydrogen or C I-$C_4$ alkyl; and mixtures thereof; wherein M is hydrogen or a water soluble cation; and X is chlorine, bromine, iodine, or other water soluble anion.

For the purposes of the present invention substituted or unsubstituted alkyleneoxy units are defined as moieties having the formula:

$$—(CH_2\overset{R^8}{\underset{|}{C}}HO)_xR^7$$

wherein $R^7$ is hydrogen; $R^8$ is hydrogen, methyl, ethyl, and mixtures thereof; the index x is from 1 to about 10.

For the purposes of the present invention substituted or unsubstituted alkyleneoxyalkyl are defined as moieties having the formula:

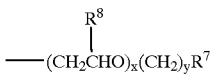

wherein $R^7$ is hydrogen, $C_1$–$C_{18}$ alkyl, $C_1$–$C_4$ alkoxy, and mixtures thereof; $R^8$ is hydrogen, methyl, ethyl, and mixtures thereof; the index x is from 1 to about 10 and the index y is from 2 to about 18.

For the purposes of the present invention substituted or unsubstituted aryl units are defined as phenyl moieties having the formula:

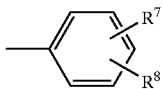

or α and β-naphthyl moieties having the formula:

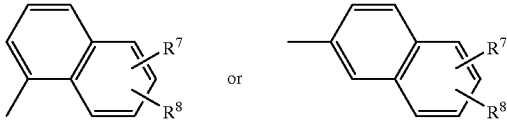

wherein $R^7$ and $R^8$ can be substituted on either ring, alone or in combination, and $R^7$ and $R^8$ are each independently hydrogen, hydroxy, $C_1$–$C_6$ alkyl, $C_2$–$C_6$ alkenyl, $C_1$–$C_4$ alkoxy, $C_3$–$C_6$ branched alkoxy, nitrilo, halogen, nitro, morpholino, cyano, carboxyl (—CHO; —$CO_2^-M^+$; —$CO_2R^9$; —$CONH_2$; —$CONHR^9$; —$CONR^9_2$; wherein $R^9$ is $C_1$–$C_{12}$ linear or branched alkyl), —$SO_3^-M^+$, —$OSO_3^-M^+$, —$N(R^{10})_2$, and —$N^+(R^{10})_3X^-$ wherein each $R^{10}$ is independently hydrogen, $C_1$–$C_4$ alkyl, or mixtures thereof; and mixtures thereof, $R^7$ and $R^8$ are preferably hydrogen, $C_1$–$C_6$ alkyl, —$CO_2^-M^+$, —$SO_3^-M^+$, —$OSO_3^-M^+$, and mixtures thereof; more preferably $R^7$ or $R^8$ is hydrogen and the other moiety is $C_1$–$C_6$; wherein M is hydrogen or a water soluble cation and X is chlorine, bromine, iodine, or other water soluble anion. Examples of other water soluble anions include organic species such as fumarate, succinate, tartrate, oxalate and the like, inorganic species include sulfate, hydrogen sulfate, phosphate and the like.

For the purposes of the present invention substituted or unsubstituted alkylenearyl units are defined as moieties having the formula:

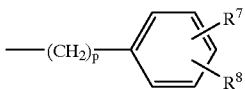

wherein $R^7$ and $R^8$ are each independently hydrogen, hydroxy, $C_1$–$C_4$ alkoxy, nitrilo, halogen, nitro, carboxyl (—CHO; —$CO_2^-M^+$; —$CO_2R^9$; —$CONH_2$; —$CONHR^9$; —$CONR^9_2$; wherein $R^9$ is $C_1$–$C_{12}$ linear or branched alkyl), amino, alkylamino, and mixtures thereof, p is from 1 to about 14; M is hydrogen or a water soluble cation.

For the purposes of the present invention substituted or unsubstituted alkyleneoxyaryl units are defined as moieties having the formula:

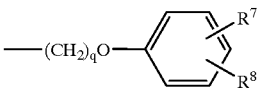

wherein $R^7$ and $R^8$ are each independently hydrogen, hydroxy, $C_1$–$C_4$ alkoxy, nitrilo, halogen, nitro, carboxyl (—CHO; —$CO_2^-M^+$; —$CO_2R^9$; —$CONH_2$; —$CONHR^9$; —$CONR^9_2$; wherein $R^9$ is $C_1$–$C_{12}$ linear or branched alkyl), amino, alkylamino, and mixtures thereof, q is from 1 to about 14; M is hydrogen or a water soluble cation.

Non-limiting examples of ketones which are releasable by the pro-accords of the fragrance delivery systems of the present invention are α-damascone, β-damascone, δ-damascone, β-damascenone, muscone, 3,3-dimethylbutanone, methyl phenyl ketone (acetophenone), 4phenylbutan-2-one (benzyl acetone), 2-acetyl-3,3-dimethyl norbomane (camek dh), 6,7-dihydro-1,1,2,3,3-pentamethyl-4(5H) indanone (cashmeran), 4-(1,3)-benzodioxol-5-yl 3-buten-2-one (cassione), 4-(3,4-methylenedioxyphenyl)-2-butanone (dulcinyl), 3-octanone, 6-acetyl-1,2,3,4-tetrahydronaphthalene ketone (florantone t), ethyl-2-n-hexyl acetoacetate (gelsone), 2,6-dimethylundeca-2,6-dien-10-one, 6,10-dimethyl-5,9-undecadien-2-one, 3,3-dimethylcyclohexyl methyl ketone (herbac), 4-(2,6,6-trimethyl-1-cyclohexen-1-yl)-3-buten-2-one (β-ionone), 4-(2,6,6-trimethyl-2-cyclohexen-1-yl)-3-buten-2-one (α-ionone), 3-methyl4(2,6,6-trimethyl-1-cyclohexen-1-yl)-3-buten-2-one (δ-methyl ionone), 4-(2,6,6-trimethyl-2-cyclohexen-1-yl)-3-methyl-3-buten-2-one (γ-methyl ionone), 3-methyl-4-(2,6,-trimethyl-2-cyclohexen-1-yl)-3-buten-2-one (irisantheme), 4-(2,3,5-trimethyl4-cyclohexen-1-yl)-3-buten-2-one (iritone), 4-methyl-(2,5,6,6-tetrarnethyl-2-cyclohexen-1-yl)3-buten-2-one (α-ionone), 1,2,3,4,5,6,7,8-octahydro-2,3,8,8-tetramethyl-2-acetonaphthone (iso cyclomone e), 7-acetyl-1,2,3,4,5,6,7,8-octahydro-1,1,6,7-tetramethyl naphthalene (Iso E Super®), acetyl diisoamylene (Koavone®), methyl amyl ketone, 2-acetonaphthone cedr-8-enyl methyl ketone (methyl cedrylone), 2,3,6-trimethyl-cyclohexen4-yl-1-methyl ketone (methyl cyclo citrone), hexahydroacetophenone (methyl cyclohexyl ketone), 6-methyl-3,5-heptadien-2-one, 6-methyl-5-hepten-2-one, 2-octanoe, 3-(hydroxymethyl)-2-nonanone, 4-acetyl- 1,1-dimethyl-6-tert-butyl indane (musk indanone), 2,6dinitro-3,5-dimethyl4-acetyl-tert-butyl benzene (musk ketone), 1-para-menthen-6-yl propanone (nerone), para-methoxy acetophenone (acetanisole), 6-acetyl-1,1,2,3,3,5-hexamethyl indan (Phantolid®), 7-acetyl- 1,1,3,4,4,6-hexamethyl tetralin (Tonalid®, Musk Plus®), 5-acetyl-3-isopropyl-1,1,2,6-tetramethyl indane (Traseolide 70®), methyl-2,6,10-trimethyl-2,5,9-cyclododecatriene-1-yl ketone (Trimofix O®), methyl cedrylone (Vertofix Coeur®), 4-(4-hydroxy-3-methoxyphenyl)-2-butanone, cis-jasmone, dihydrojasmone, α-ionone, β-ionone, dihydro-β-ionone, 4-(4-hydroxyphenyl)butan-2-one, 1-carvone, 5-cyclohexadecen-1-one, decatone, 2-[2-(4-methyl-3-cyclohexenyl-1-yl) propyl]cyclopentan-2-one, 2-sec-butylcyclohexanone, allyl ionone, α-cetone, geranyl acetate, 1-(2-methyl-5-isopropyl-2-cyclohexenyl)-1-propanone, acetyl diisoamylene, methyl cyclocitrone, 4-t-pentyl cyclohexanone, p-t-butylcyclohexanone, o-t-butylcyclohexanone, menthone, methyl-7,3-dihydro-2H-1,5-benzodioxepine-3-one, fenchone, methyl hydroxynaphthyl ketone, and mixtures thereof.

According to the present invention all isomers of a fragrance raw material whether in the form of the pro-fragrance or the released fragrance raw material, are suitable for use in the present invention. When optical isomers are possible, fragrance raw materials may be included as either the separate chemical isomer or as the combined racemic mixture. For example, 3,7-dimethyl-6-octen-1-ol, commonly known by those of ordinary skill in the art as β-citronellol or cephrol, comprises a pair of optical isomers, R—(+)-β-citronellol and S—(−)-β-citronellol. Each of these materials separately or as a racemic pair are suitable for use as fragrance raw materials in the present invention. However, those skilled in the art of fragrances, by utilization of the present invention, should not disregard the olfactory differences that individual optical isomers, admixtures of optical isomers or admixtures of positional isomers imparl By way of example, carvone, 2-methyl-5-(1-methylethenyl)-2-cyclohexene-1-one exists as two isomers; d-carvone and l-carvone. d-Carvone is found in oil of caraway and renders a completely different fragrance from l-carvone which is found in spearmint oil. According to the present invention a pro-fragrance which releases d-carvone will result in a different scent or fragrance than one which releases l-carvone. The same applies to l-carvone. In addition, isomers such as cis/trans isomers, for example, nerol (3,7-dimethyl-cis-2,6-octadien-1-ol) and geraniol (3,7-dimethyl-trans-2,6-octadien-1-ol), are well known to those skilled in the art of perfumery and these two terpene alcohols, which commonly occur as an admixture, have different fragrance characteristics. Therefore, when formulating fragrance raw materials which comprise mixtures of isomers such as nerol/geraniol, the formulator must also take into account whether different sources of raw material have different ratios of isomers.

An example of a preferred pro-fragrance is 3,7-dimethyl-1,6-octadien-3-yl 3-(β-naphthyl)-3oxo-propionate having the formula:

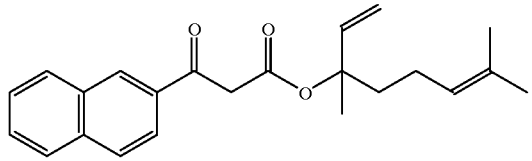

which releases at least the fragrance raw material alcohol, linalool, having the formula:

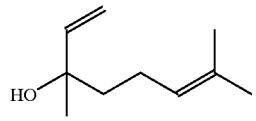

and the fragrance raw material ketone, methyl naphthyl ketone, having the formula:

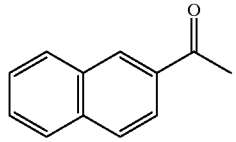

A further example of a preferred pro-fragrance includes 2,6-dimethyl-7-octen-2-yl 3-(4-methoxyphenyl)3-oxo-propionate having the formula:

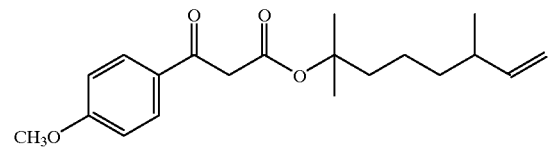

which releases at least the fragrance raw material alcohol, dihydromyrcenol, having the formula:

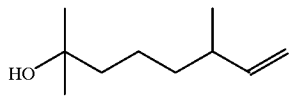

and the fragrance raw material ketone, methyl 4methoxyphenyl ketone, having the formula:

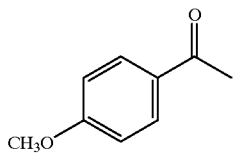

Further non-limiting examples of preferred pro-fragrances include 3,7-dimethyl- 1,6-octadien-3-yl 3-(α-naphthyl)-3-oxo-propionate, [linalyl (1 -naphthoyl)acetate], having the formula:

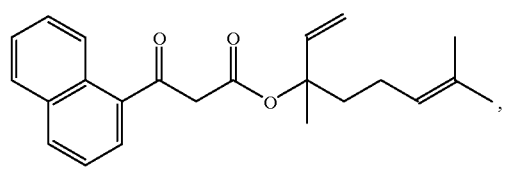

2,6-dimethyl-7-octen-2-yl 3-(4-methoxyphenyl)-3-oxo-propionate, [3-(4-methoxyphenyl)-3-oxo-propionic acid dihydromyrcenyl ester], having the formula:

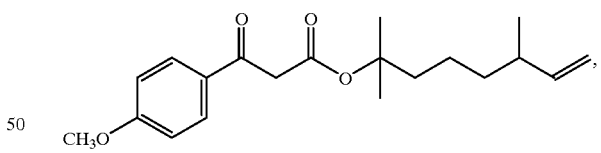

2,6-dimethyl-7-octen-2-yl 3-(4-nitrophenyl)-3-oxo-propionate, [3-(4-nitrophenyl)-3-oxo-propionic acid dihydromyrcenyl ester], having the formula:

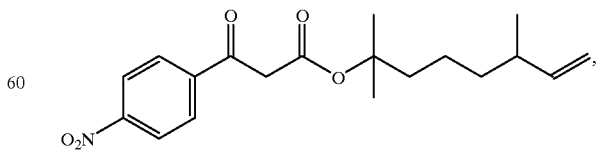

2,6-dimethyl-7-octen-2-yl 3-(β-naphthyl)-3-oxo-propionate, [dihydromyrcenyl (2-naphthoyl)acetate], having the formula:

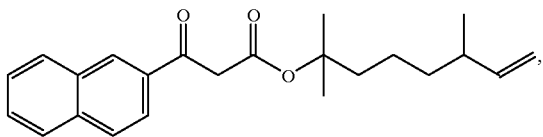

3,7-dimethyl-1,6octadien-3-yl 3-(4-methoxyphenyl)-3-oxo-propionate, [3-(4-methoxyphenyl)-3-oxo-propionic acid linalyl ester], having the formula:

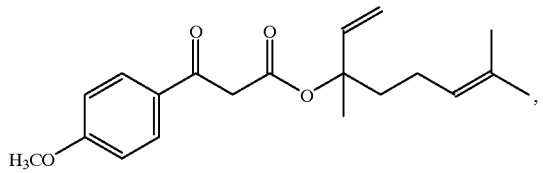

(α,α-4-timethyl-3-cyclohexenyl)methyl 3-(β-naphthyl)-3-oxo-propionate, [α-terpinyl (2-naphthoyl)acetate], having the formula:

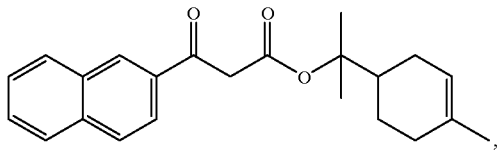

9-decen-1-yl 3-(naphthyl)-3-oxo-propionate, [9-decen-1-yl (2-naphthoyl)acetate], known alternatively as, rosalva 2'-acetonaphthone, having the formula:

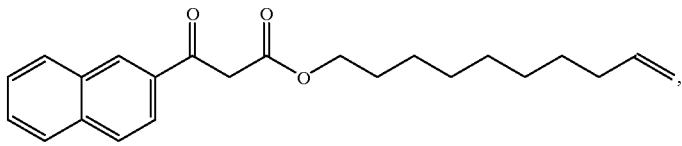

3,7-dimethyl-1,6-octadien-3-yl 3-(nonanyl)-3-oxo-propionate, [linalyl (nonanoyl)acetate], known alternatively as, octyl [(linalyl) α-acetyl] ketone, having the formula:

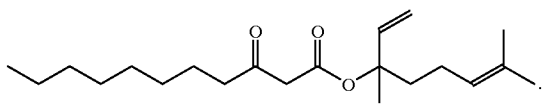

Additional non-limiting examples of preferred pro-fragrances which comprise the fragrance delivery systems of the present invention include cis 3-hexen-1-yl 3-(β-naphthyl)-3-oxo-propionate, 2,6-dimethyl-7-octen-2-yl 3-(nonanyl)-3-oxo-propionate, 2,6dimethyl-7-octen-2-yl 3-oxo-butyrate, 3,7-dimethyl-1,6-octadien-3-yl 3-oxo-butyrate, 2,6-dimethyl-7-octen-2-yl 3-(β-naphthyl)-3-oxo-2-methylpropionate, 3,7-dimethyl-1,6-octadien-3-yl 3-(β-naphthyl)-3-oxo-2,2-dimethylpropionate, 3,7-dimethyl-1,6-octadien-3-yl 3-(β-naphthyl)-3-oxo-2-methylpropionate, 3,7-dimethyl-2,6-octadienyl 3-(β-naphthyl)-3-oxo-propionate, 3,7-dimethyl-2,6-octadienyl 3-heptyl-3-oxo-propionate, and mixtures thereof.

The formulator is not limited to the delivery of one type of fragrance, for example a top, middle, or base fragrance raw material note. Instead a mixture of top notes, a mixture of top and middle notes, or any combination of top, middle and base notes may be delivered in any suitable proportion. As described herein above, those skilled in the art of preparing fragrance- containing compositions have categorized fragrances into three types based on their relative volatility; top, middle, and base notes. In addition, fragrances are categorized by the odor they produce; some of these descriptors are broad and others are relatively specific. For example, "floral" is a term which connotes odors associated with flowers while the term "lilac" is more specific. Descriptors used by those skilled in the art of perfiumes and fragrances are inter alia "rose", "floral", "green", "citrus", "spicy", "honey", and "musk". The sources of these notes are not limited to one chemical class; alcohols can produce "rose", "green", and "musk" scents, while "rose" scents can comprise alcohols, ketones, terpenes, aldehydes, etc.

Top, middle, and base notes each serve a different purpose in the blending of fragrances and when properly formulated produce a "balanced fragrance" composition. Based on volatility, these notes are described by those skilled in the art as: the base notes having the most long lasting aroma; the middle notes, have a medium volatility; and the top notes are the most volatile. The compositions described herein below, as well as others chosen by the formulator, comprise a fragrance delivery system which utilizes the pro-fragrances of the present invention to successfully deliver a "balanced fragrance" profile.

It is also recognized by those skilled in the art that descriptors which relate to aesthetic perceptions such as "top", "middle" and "base" notes are relative terms. A fragrance raw material categorized as a top note by one formulator usually has the identical classification among most other Perfiuners. The same is true for the middle and base notes, however, occasionally one formulator may classify a given fragrance raw material as a middle note rather than a top note, or vice versa, but this fact does not diminish the utility of a given compound or its absolute identity. Top, middle and base notes are now combined in a reproducible manner to produce perfumes, colognes, after-shave lotions, eau de toilettes, etc. for application to skin, which have unique and pleasant odor characteristics. Yet apart from this pleasant fragrance, a fragrance delivery system which is used to deliver a scent to a laundry detergent composition must meet a number of technical requirements. It must be sufficiently strong, it must be persistent, and it must retain its "essential character" throughout its period of evaporation and fragrance raw material release.

Aside from the changes made to the "pro-fragrance" molecules for the purpose of modifying the fragrance profiles which the fragrance delivery systems of the present invention provide, modifications can be made to these pro-fragrances for the purpose of increasing the substantivity of the materials. The formulator by selecting a suitable $R^1$, $R^2$, or $R^3$ unit, or upon the selection of $R^4$ $R^5$, and $R^6$, can influence the degree and rate at which the "pro-fragrance" is deposited upon fabric or other surface. Those skilled in the art of formulating detergent compositions will recognize that the terms "substantive" and "substantivity" refer to the propensity of a compound to adhere to, associate with, or deposit upon a surface, preferably the surface of fabric. Therefore, compounds which are more substantive more readily adhere to fabric surface. However, substantive compounds, in general, do not react with the surface onto which they deposit.

An example of a pro-fragrance which is modified to provide higher fabric substantivity is the 2,6-dimethyl-7-octen-2-yl 3-(β-naphthyl)-2-(methoxy-pentaethyleneoxy)-3-oxo-propionate, [dihydromyrcenyl (2-naphthoyl)(2-$E_5$ methoxy)acetate], having the formula:

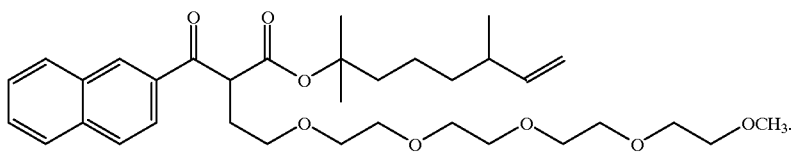

In addition to substitution at the a-carbon atom, substitution can be made at other sites of the pro-accord molecule, for example, 3,7-dimethyl- 1,6-octadien-3-yl 3-(methoxy triethyleneoxy)3-oxo-butyrate, [linalyl (methoxy $E_3$)acetate] having the formula:

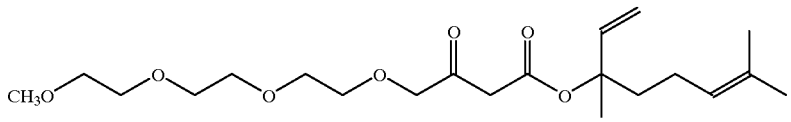

is a pro-fragrance modified to increase fabric substantivity.

Surfactant systems

The instant liquid laundry detergent compositions may contain at least about 0.01 % by weight of a surfactant selected from the group consisting of anionic, cationic, nonionic, ampholytic and zwitterionic surface active agents. Preferably the surfactant, is present to the extent of from about 0.1% to 60%, more preferably 0.1% to about 30% by weight of the composition.

Nonlimiting examples of surfactants useful herein typically at levels from about 1% to about 55%, by weight, include the conventional $C_{11}$–$C_{18}$ alkyl benzene sulfonates ("LAS") which is a preferred surfactant and primary, branched-chain and random $C_{10}$–$C_{20}$ alkyl sulfates ("AS"), the $C_{10}$–$C_{18}$ secondary (2,3) alkyl sulfates of the formula $CH_3(CH_2)x(CHOSO_3^-M^+)$ $CH_3$ and $CH_3$ $(CH_2)_y$ $(CHOSO_3^-M^+)$ $CH_2CH_3$ where x and (y+1) are integers of at least about 7, preferably at least about 9, and M is a water-solubilizing cation, especially sodium, unsaturated sulfates such as oleyl sulfate, the $C_{10}$–$C_{18}$ alkyl alkoxy sulfates ("$AE_xS$"; especially EO 1-7 ethoxy sulfates), $C_{10}$–$C_{18}$ alkyl alkoxy carboxylates (especially the EO 1-5 ethoxycarboxylates), the $C_{10-18}$ glycerol ethers, the $C_{10}$–$C_{18}$ alkyl polyglycosides and their corresponding sulfated polyglycosides, and $C_{12}$–$C_{18}$ alpha-sulfonated fatty acid esters. If desired, the conventional nonionic and amphoteric surfactants such as the $C_{12}$–$C_{18}$ alkyl ethoxylates ("AE") including the so-called narrow peaked alkyl ethoxylates and $C_6$–$C_{12}$ alkyl phenol alkoxylates (especially ethoxylates and mixed ethoxy/propoxy), $C_{12}$–$C_{18}$ betaines and sulfobetaines ("sultaines"), $C_{10}$–$C_{18}$ amine oxides, and the like, can also be included in the overall compositions. The $C_{10}$–$C_{18}$ N-alkyl polyhydroxy fatty acid amides are highly preferred, especially the $C_{12}$–$C_{18}$ N-methylglucamnides. See WO 9,206,154. Other sugar-derived surfactants include the N-alkoxy polyhydroxy fatty acid amides, such as $C_{10}$–$C_{18}$ N-(3-methoxypropyl) glucamide. The N-propyl through N-hexyl $C_{12}$–$C_{18}$ glucamides can be used for low sudsing. $C_{10}$–$C_{20}$ conventional soaps may also be used. If high sudsing is desired, the branched-chain $C_{10}$–$C_{16}$ soaps may be used. Mixtures of anionic and nonionic surfactants are especially useful. Other conventional useful surfactants are described further herein and are listed in standard texts.

Anionic surfactants can be broadly described as the water-soluble salts, particularly the aLkali metal salts, of organic suluic reaction products having in their molecular structure an alkyl radical containing from about 8 to about 22 carbon atoms and a radical selected from the group consisting of sulfonic acid and suluic acid ester radicals. ( Included in the term alkyl is the alkyl portion of higher acyl radicals.) Important examples of the anionic synthetic detergents which can form the surfactant component of the compositions of the present invention are the sodium or potassium alkyl sulfates, especially those obtained by sulfating the higher alcohols (C8–18 carbon atoms) produced by reducing the glycerides of tallow or coconut oil; sodium or potassium alkyl benzene sulfonates, in which the alkyl group contains from about 9 to about 15 carbon atoms, (the alkyl radical can be a straight or branched aliphatic chain); sodium alkyl glyceryl ether sulfonates, especially those ethers of the higher alcohols derived from tallow and coconut oil; sodium coconut oil fatty acid monoglyceride sulfates and sulfonates; sodium or potassium salts of sulfuric acid ester of the reaction product of one mole of a higher fatty alcohol (e.g. tallow or coconut alcohols) and about 1 to about 10 moles of ethylene oxide; sodium or potassium salts of alkyl phenol ethylene oxide ether sulfates with about 1 to about 10 units of ethylene oxide per molecule and in which the alkyl radicals contain fiom 8 to 12 carbon atoms; the reaction products of fatty acids are derived from coconut oil sodium or potassium salts of fatty acid amides of a methyl tauride in which the fatty acids, for example, are derived from coconut oil and sodium or potassium beta-acetoxy- or beta-acetamido-alkanesulfonates where the alkane has from 8 to 22 carbon atoms.

Additionally, secondary alkyl sulfates may be used by the formulator exclusively or in conjunction with other surfactant materials and the following identifies and illustrates the differences between sulfated surfactants and otherwise conventional alkyl sulfate surfactants. Non-limiting examples of such ingredients are as follows.

Conventional primary alkyl sulfates (AS), such as those illustrated above, have the general formula ROSO3–M+ wherein R is typically a linear C8–22 hydrocarbyl group and M is a water solublizing cation. Branched chain primary alkyl sulfate surfactants (i.e., branched-chain "PAS") having 8–20 carbon atoms are also know; see, for example, Eur. Pat. Appl 439,316, Smith et al., filed Jan. 21, 1991.

Conventional secondary alkyl sulfate surfactants are those materials which have the sulfate moiety distributed randomly along the hydrocarbyl "backbone" of the molecule. Such materials may be depicted by the structure

wherein m and n are integers of 2 of greater and the sum of m+n is typically about 9 to 17, and M is a water-solublizing cation.

The aforementioned secondary alkyl sulfates are those prepared by the addition of $H_2SO_4$ to olefins. A typical synthesis using alpha olefins and sulfuric acid is disclosed in U.S. Pat. No. 3,234,258, Morris, issued Feb. 8, 1966 or in U.S. Pat. No. 5,075,041, Lutz, issued Dec. 24, 1991. See also U.S. Pat. No. 5,349,101, Lutz et al., issued Sep. 20, 1994; U.S. Pat. No. 5,389,277, Prieto, issued Feb. 14, 1995.

The preferred surfactants of the present invention are anionic surfactants, however, other surfactants usefuil herein are described below.

The compositions of the present invention can also comprise at least about 0.01%, preferably at least 0.1%o, more preferably from about 1% to about 30%, of an nonionic detersive surfactant. Preferred nonionic surfactants such as $C_{12}$–$C_{18}$ alkyl ethoxylates ("AE") including the so-called narrow peaked alkyl ethoxylates and $C_6$–$C_{12}$ alkyl phenol alkoxylates (especially ethoxylates and mixed ethoxy/propoxy), block alkylene oxide condensate of $C_6$ to $C_{12}$ alkyl phenols, alkylene oxide condensates of $C_8$–$C_{22}$ alkanols and ethylene oxide/propylene oxide block polymers (Pluronic™-BASF Corp.), as well as semi polar non-ionics (e.g., amine oxides and phosphine oxides) can be used in the present compositions. An extensive disclosure of these types of surfactants is found in U.S. Pat. No. 3,929,678, Laughlin et al., issued Dec. 30, 1975, incorporated herein by reference.

Alkylpolysaccharides such as disclosed in U.S. Pat. No. 4,565,647 Llenado (incorporated herein by reference) are also preferred nonionic surfactants in the compositions of the invention.

More preferred nonionic surfactants are the polyhydroxy fatty acid amides having the formula:

wherein $R^7$ is $C_5$–$C_{31}$ alkyl, preferably straight chain $C_7$–$C_{19}$ alkyl or alkenyl, more preferably straight chain $C_9$–$C_{17}$ alkyl or alkenyl, most preferably straight chain $C_{11}$–$C_{15}$ alkyl or alkenyl, or mixtures thereof; $R^8$ is selected from the group consisting of hydrogen, $C_1$–$C_4$ alkyl, $C_1$–$C_4$ hydroxyalkyl, preferably methyl or ethyl, more preferably methyl. Q is a polyhydroxyalkyl moiety having a linear alkyl chain with at least 3 hydroxyls directly connected to the chain, or an alkoxylated derivative thereof; preferred alkoxy is ethoxy or propoxy, and mixtures thereof. Preferred Q is derived from a reducing sugar in a reductive amination reaction. More preferably Q is a glycityl moiety. Suitable reducing sugars include glucose, fructose, maltose, lactose, galactose, mannose, and xylose. As raw materials, high dextrose corn syrup, high fructose corn syrup, and high maltose corn syrup can be utilized as well as the individual sugars listed above. These corn syrups may yield a mix of sugar components for Q. It should be understood that it is by no means intended to exclude other suitable raw materials. Q is more preferably selected from the group consisting of —$CH_2(CHOH)_nCH_2OH$, —$CH(CH_2OH)(CHOH)_{n-1}CH_2OH$, —$CH_2(CHOH)_2$-$(CHOR')(CHOH)CH_2OH$, and alkoxylated derivatives thereof, wherein n is an integer from 3 to 5, inclusive, and R' is hydrogen or a cyclic or aliphatic monosaccharide. Most preferred substituents for the Q moiety are glycityls wherein n is 4, particularly —$CH_2(CHOH)_4CH_2OH$.

$R^7CO$—N<can be, for example, cocamide, stearamide, oleamide, lauramide, myristamide, capricamide, palmitamide, tallowamide, etc.

$R^8$ can be, for example, methyl, ethyl, propyl, isopropyl, butyl, 2-hydroxy ethyl, or 2-hydroxy propyl.

Q can be 1-deoxyglucityl, 2-deoxyfructityl, 1-deoxymaltityl, 1-deoxylactityl, 1-deoxygalactityl, 1-deoxymannityl, 1-deoxymaltotriotityl, etc.

A particularly desirable surfactant of this type for use in the compositions herein is alkyl-N-methyl glucomide, a compound of the above formula wherein $R^7$ is alkyl (preferably $C_{11}$–$C_{17}$), $R^8$, is methyl and Q is 1-deoxyglucityl.

Other sugar-derived surfactants include the N-alkoxy polyhydroxy fatty acid amides, such as $C_{10}$–$C_{18}$ N—(3-methoxypropyl) glucamide. The N-propyl through N-hexyl $C_{12}$–$C_{18}$ glucamides can be used for low sudsing. $C_{10}$–$C_{20}$ conventional soaps may also be used. If high sudsing is desired, the branched-chain $C_{10}$–$C_{16}$ soaps may be used.

Enzymes

Protease Enzvmes

The preferred liquid laundry detergent compositions according to the present invention further comprise at least 0.001% by weight, of a protease enzyme. However, an effective amount of protease enzyme is sufficient for use in the liquid laundry detergent compositions described herein. The term "an effective amount" refers to any amount capable of producing a cleaning, stain removal, soil removal, whitening, deodorizing, or freshness improving effect on substrates such as fabrics. In practical terms for current commercial preparations, typical amounts are up to about 5 mg by weight, more typically 0.01 mg to 3 mg, of active enzyme per gram of the detergent composition. Stated otherwise, the compositions herein will typically comprise from 0.001% to 5%, preferably 0.01%–1% by weight of a commercial enzyme preparation. The protease enzymes of the present invention are usually present in such commercial preparations at levels sufficient to provide from 0.005 to 0.1 Anson units (AU) of activity per gram of composition.

Preferred liquid laundry detergent compositions of the present invention comprise modified protease enzymes derived from *Bacillus amyloliquefaciens* or *Bacillus lentus*. For the purposes of the present invention, protease enzymes derived from *B. amyloliquefaciens* are fijrther referred to as "subtilisin BPN" also referred to as "Protease A" and protease enzymes derived from *B. Lentus* are further referred to as "subtilisin 309". For the purposes of the present invention, the numbering of *Bacillus amyloliquefaciens* subtilisin, as described in the patent applications of A. Baeck, et al, entitled "Protease-Containing Cleaning Compositions" having U.S. Ser. No. 08/322,676, serves as the amino acid sequence numbering system for both subtilisin BPN' and subtilisin 309.

Derivatives of *Bacillus amyloliquefaciens* subtilisin -BPN' enzymes

Bleach Stable Variants of BPN' (Protease A-BSV)

A preferred protease enzyme for use in the present invention is a bleach stable variant of Protease A (BPN'). This bleach stable variant of BPN' is a non-naturally occurring carbonyl hydrolase variant having a different proteolytic activity, stability, substrate specificity, pH profile and/or performance characteristic as compared to the precursor carbonyl hydrolase from which the amino acid sequence of the variant is derived. This bleach stable variant of BPN' is disclosed in EP 130,756 A, Jan. 9, 1985. Specifically Protease A-BSV is BPN' wherein the Gly at position 166 is replaced with Asn, Ser, Lys, Arg, His, Gln, Ala, or Glu; the Gly at position 169 is replaced with Ser; the Met at position 222 is replaced with Gln, Phe, Cys, His, Asn, Glu, Ala or Thr; or alternatively the Gly at position 166 is replaced with Lys, and the Met at position 222 is replaced with Cys; or alternatively the Gly at position 169 is replaced with Ala and the Met at position 222 is replaced with Ala.

Protease B A preferred protease enzyme for use in the present invention is Protease B. Protease B is a non-naturally occurring carbonyl hydrolase variant having a different proteolytic activity, stability, substrate specificity, pH profile and/or performance characteristic as compared to the precursor carbonyl hydrolase from which the amino acid sequence of the variant is derived. Protease B is a variant of BPN' in which tyrosine is replaced with leucine at position +217 and as further disclosed in EP 303,761 A, Apr. 28, 1987 and EP 130,756 A, Jan. 9, 1985.

Bleach Stable Variants of Protease B (Protease B-BSV)

A preferred protease enzyme for use in the present invention are bleach stable variants of Protease B. Specifically Protease B-BSV are variants wherein the Gly at position 166 is replaced with Asn, Ser, Lys, Arg, His, Gln, Ala, or Glu; the Gly at position 169 is replaced with Ser; the Met at position 222 is replaced with Giln, Phe, Cys, His, Asn, Glu, Ala or Thr; or alternatively the Gly at position 166 is replaced with Lys, and the Met at position 222 is replaced with Cys; or alternatively the Gly at position 169 is replaced with Ala and the Met at position 222 is replaced with Ala.

Surface Active Variants of Protease B

Preferred Surface Active Variants of Protease B comprise BPN' wild-type amino acid sequence in which tyrosine is replaced with leucine at position +217, wherein the wild-type amino acid sequence at one or more of positions 199, 200, 201, 202, 203, 204, 205, 206, 207, 208, 209, 210, 211, 212, 213, 214, 215, 216, 218, 219 or 220 is substituted; wherein the BPN' variant has decreased adsorption to, and increased hydrolysis of, an insoluble substrate as compared to the wild-type subtilisin BPN'. Preferably, the positions having a substituted amino acid are 199, 200, 201, 202, 205, 207, 208, 209, 210, 211, 212, or 215; more preferably, 200, 201, 202, 205 or 207.

Also preferred proteases derived from *Bacillus amyloliquefaciens* subtilisin are subtilisin BPN' enzymes that have been modified by mutating the various nucleotide sequences that code for the enzyme, thereby modifying the amino acid sequence of the enzyme. These modified subtilisin enzymes have decreased adsorption to and increased hydrolysis of an insoluble substrate as compared to the wild-type subtilisin. Also suitable are mutant genes encoding for such BPN' variants.

Derivatives of subtilisin 309

Further preferred protease enzymes for use according to the present invention also include the "subtilisin 309" variants. These protease enzymes include several classes of subtilisin 309 variants described herein below.

Protease D

A preferred protease enzyme for use in the present invention is Protease D. Protease D is a carbonyl hydrolase variant derived from *Bacillus lentus* subtilisin having an amino acid sequence not found in nature, which is derived from a precursor carbonyl hydrolase by substituting a different amino acid for a plurality of amino acid residues at a position in said carbonyl hydrolase equivalent to position +76, preferably also in combination with one or more amino acid residue positions equivalent to those selected from the group consisting of +99, +101, +103, +104, +107, +123, +27, +105, +109, +126, +128, +135, +156, +166, +195, +197, +204, +206, +210, +216, +217, +218, +222, +260, +265, and/or +274 according to the numbering of *Bacillus amyloliquefaciens* subtilisin, as described in WO 95/10615 published Apr. 20, 1995 by Genencor International.

A. Loop Region 6 Substitution Variants—These subtilisin 309-type variants have a modified amino acid sequence of subtilisin 309 wild-type amino acid sequence, wherein the modified amino acid sequence comprises a substitution at one or more of positions 193, 194, 195, 196, 197, 199, 200, 201, 202, 203, 204, 205, 206, 207, 208, 209, 210, 211, 212, 213 or 214; whereby the subtilisin 309 variant has decreased adsorption to, and increased hydrolysis of, an insoluble substrate as compared to the wild-type subtilisin 309. Preferably these proteases have amino acids substituted at 193, 194, 195, 196, 199, 201, 202, 203, 204, 205, 206 or 209; more preferably 194, 195, 196, 199 or 200.

B. Multi-Loop Regions Substitution Variants—These subtilisin 309 variants may also be a modified amino acid sequence of subtilisin 309 wild-type amino acid sequence, wherein the modified amino acid sequence comprises a substitution at one or more positions in one or more of the first, second, third, fourth, or fifth loop regions; whereby the subtilisin 309 variant has decreased adsorption to, and increased hydrolysis of, an insoluble substrate as compared to the wild-type subtilisin 309.

C. Substitutions at positions other than the loop regions— In addition, one or more substitution of wild-type subtilisin 309 may be made at positions other than positions in the loop regions, for example, at position 74. If the additional substitution to the subtilisin 309 is mad at position 74 alone, the substitution is preferably with Asn, Asp, Glu, Gly, His, Lys, Phe or Pro, preferably His or Asp. However modifications can be made to one or more loop positions as well as position 74, for example residues 97, 99, 101, 102, 105 and 121.

Subtilisin BPN' variants and subtilisin 309 variants are firther described in WO 95/29979, WO 95/30010 and WO 95/30011, all of which were published Nov. 9, 1995, all of which are incorporated herein by reference.

A fuirther preferred protease enzyme for use in combination with the modified polyamines of the present invention is ALCALASE® from Novo. Another suitable protease is obtained from a strain of Bacillus, having maximum activity throughout the pH range of 8–12, developed and sold as ESPERASE® B by Novo Industries A/S of Dernmark, hereinafter "Novo". The preparation of this enzyme and analogous enzymes is described in GB 1,243,784 to Novo. Other suitable proteases include SAVINASE® from Novo and MAXATASE® from International Bio-Synthetics, Inc., The Netherlands. See also a high pH protease from Bacillus sp. NCIMB 40338 described in WO 9318140 A to Novo. Enzymatic detergents comprising protease, one or more other enzymes, and a reversible protease inhibitor are described in WO 9203529 A to Novo. Other preferred proteases include those of WO 9510591 A to Procter &

Gamble. When desired, a protease having decreased adsorption and increased hydrolysis is available as described in WO 9507791 to Procter & Gamble. A recombinant trypsin-like protease for detergents suitable herein is described in WO 9425583 to Novo.

In addition to the above-described protease enzyme, other enzymes suitable for use in the liquid laundry detergent compositions of the present invention are furter described herein below.

Other Enymes

Enzymes in addition to the protease enzyme can be included in the present detergent compositions for a variety of purposes, including removal of protein-based, carbohydrate-based, or triglyceride-based stains from surfaces such as textiles, for the prevention of refugee dye transfer, for example in laundering, and for fabric restoration. Suitable enzymes include proteases, amylases, lipases, cellulases, peroxidases, and mixtures thereof of any suitable origin, such as vegetable, animal, bacterial, fumgal and yeast origin. Preferred selections are influenced by factors such as pH-activity and/or stability optima, thermostability, and stability to active detergents, builders. and the like. In this respect bacterial or fangal enzymes are preferred, such as bacterial amylases and proteases, and fungal cellulases.

"Detersive enzyme", as used herein, means any enzyme having a cleaning, stain removing or otherwise beneficial effect in a liquid laundry, hard surface cleaning or personal care detergent composition. Preferred detersive enzymes are hydrolases such as proteases, amylases and lipases. Preferred enzymes for liquid laundry purposes include, but are not limited to, proteases, cellulases, lipases and peroxidases.

Enzymes are normally incorporated into detergent or detergent additive compositions at levels sufficient to provide a "cleaning-effective amount". The term "cleaning effective amount" refers to any amount capable of producing a cleaning, stain removal, soil removal, whitening, deodorizing, or freshness improving effect on substrates such as fabrics. In practical terms for current commercial preparations, typical amounts are up to about 5 mg by weight, more typically 0.01 mg to 3 mg, of active enzyme per gram of the detergent composition. Stated otherwise, the compositions herein will typically comprise from 0.001% to 5%, preferably 0.01%–1% by weight of a commercial enzyme preparation. Protease enzymes are usually present in such commercial preparations at levels sufficient to provide from 0.005 to 0.1 Anson units (AU) of activity per gram of composition. For certain detergents, it may be desirable to increase the active enzyme content of the commercial preparation in order to minimize the total amount of non-catalytically active materials and thereby improve spotting/filming or other end-results. Higher active levels may also be desirable in highly concentrated detergent formulations.

Amylases suitable herein include, for example, α-amylases described in GB 1,296,839 to Novo; RAPIDASE®, International Bio-Synthetics, Inc. and TERMAMYL®, Novo. FUNGAMYL® from Novo is especially useful. Engineering of enzymes for improved stability, e.g., oxidative stability, is known. See, for example J. Biological Chem., Vol. 260, No. 11, June 1985, pp 6518–6521. Certain preferred embodiments of the present compositions can make use of amylases having improved stability in detergents, especially improved oxidative stability as measured against a reference-point of TERMAMYL® in commercial use in 1993. These preferred amylases herein share the characteristic of being "stability-enhanced" amylases, characterized, at a minimum, by a measurable improvement in one or more of: oxidative stability, e.g., to hydrogen peroxide/tetraacetylethylenediamine in buffered solution at pH 9–10; thermal stability, e.g., at common wash temperatures such as about 60° C.; or alkaline stability, e.g., at a pH from about 8 to about 11, measured versus the above-identified reference-point amylase. Stability can be measured using any of the art-disclosed technical tests. See, for example, references disclosed in WO 9402597. Stability-enhanced amylases can be obtained from Novo or from Genencor International. One class of highly preferred amylases herein have the commonality of being derived using site-directed mutagenesis from one or more of the Baccillus amylases, especialy the *Bacillus a*-amylases, regardless of whether one, two or multiple amylase strains are the immediate precursors. Oxidative stability-enhanced amylases vs. the above- identified reference amylase are preferred for use, especially in bleaching, more preferably oxygen bleaching, as distinct from chlorine bleaching, detergent compositions herein. Such preferred amylases include (a) an amylase according to the hereinbefore incorporated WO 9402597, Novo, Feb. 3, 1994, as further illustrated by a mutant in which substitution is made, using alanine or threonine, preferably threonine, of the methionine residue located in position 197 of the *B. licheniformis* alpha-amylase, known as TERIAMYL®, or the homologous position variation of a similar parent amnylase, such as *B. amyloliquefaciens, B. subtilis*, or *B.stearothermophilus*; (b) stability-nhanced amylases as described by Genencor International in a paper entitled "Oxidatively Resistant alpha-Amylases" presented at the 207th American Chemical Society National Meeting, Mar. 13–17 1994, by C. Mitchinson. Therein it was noted that bleaches in automatic dishwashing detergents inactivate alpha-amylases but that improved oxidative stability amylases have been made by Genencor from *B. licheniformis* NCIB8061. Methionine (Met) was identified as the most likely residue to be modified. Met was substituted, one at a time, in positions 8, 15, 197, 256, 304, 366 and 438 leading to specific mutants, particularly important being M197L and M197T with the M197T variant being the most stable expressed variant. Stability was measured in CASCADE® and SUNLIGHT®; (c) particularly preferred amylases herein include amylase variants having additional modification in the immediate parent as described in WO 9510603 A and are available from the assignee, Novo, as DURAMYL®. Other particularly preferred oxidative stability enhanced amylase include those described in WO 9418314 to Genencor International and WO 9402597 to Novo. Any other oxidative stability-enhanced amylase can be used, for example as derived by site-directed mutagenesis from known chimeric, hybrid or simple mutant parent forms of available amylases. Other preferred enzyme modifications are accessible. See WO 9509909 A to Novo.

Cellulases usable herein include both bacterial and flngal types, preferably having a pH optimum between 5 and 9.5. U.S. Pat. No. 4,435,307, Barbesgoard et al, Mar. 6, 1984, discloses suitable fungal cellulases from *Humicola insolens* or Humicola strain DSM1800 or a cellulase 212-producing fungus belonging to the genus Aeromonas, and cellulase extracted from the hepatopancreas of a marine mollusk, *Dolabella Auricula Solander*. Suitable cellulases are also disclosed in GB-A-2.075.028; GB-A-2.095.275 and DE-OS-2.247.832. CAREZYME® (Novo) is especially useful. See also WO 9117243 to Novo.

Suitable lipase enzymes for detergent usage include those produced by microorganisms of the Pseudomonas group, such as *Pseudomonas stutzeri* ATCC 19.154, as disclosed in GB 1,372,034. See also lipases in Japanese Patent Application 53,20487, laid open Feb. 24, 1978. This lipase is available from Amano Pharmaceutical Co. Ltd., Nagoya, Japan, under the trade name Lipase P "Amano," or "Amano-P." Other suitable commercial lipases include Amano-CES, lipases ex *Chromobacter viscosum*, e.g. *Chromobacter viscosum* var. lipolyticum NRRLB 3673 from Toyo Jozo Co., Tagata, Japan; *Chromobacter viscosum* lipases from U.S. Biochemical Corp., U.S.A. and Disoynth Co., The Netherlands, and lipases ex *Pseudomonas gladioli*. LIPO-LASE® enzyme derived from *Humicola lanuginosa* and commercially available from Novo, see also EP 341,947, is a preferred lipase for use herein. Lipase and amylase variants stabilized against peroxidase enzymes are described in WO 9414951 A to Novo. See also WO 9205249 and RD 94359044.

Cutinase enzymes suitable for use herein are described in WO 8809367 A to Genencor.

Peroxidase enzymes may be used in combination with oxygen sources, e.g., percarbonate, perborate, hydrogen peroxide, etc., for "solution bleaching" or prevention of transfer of dyes or pigments removed from substrates during the wash to other substrates present in the wash solution. Known peroxidases include horseradish peroxidase, ligninase, and haloperoxidases such as chloro- or bromo-peroxidase. Peroxidase-containing detergent compositions are disclosed in WO 89099813 A, Oct. 19, 1989 to Novo and WO 8909813 A to Novo.

A range of enzyme materials and means for their incorporation into synthetic detergent compositions is also disclosed in WO 9307263 A and WO 9307260 A to Genencor International, WO 8908694 A to Novo, and U.S. Pat. No. 3,553,139, Jan. 5, 1971 to McCarty et al. Enzymes are further disclosed in U.S. Pat. No. 4,101,457, Place et al, Jul. 18, 1978, and in U.S. Pat. No. 4,507,219, Hughes, Mar. 26, 1985. Enzyme materials useful for liquid detergent formulations, and their incorporation into such formulations, are disclosed in U.S. Pat. No. 4,261,868, Hora et al, Apr. 14, 1981. Enzymes for use in detergents can be stabilized by various techniques. Enzyme stabilization techniques are disclosed and exemplified in U.S. Pat. No. 3,600,319, Aug. 17, 1971, Gedge et al, EP 199,405 and EP 200,586, Oct. 29, 1986, Venegas. Enzyme stabilization systems are also described, for example, in U.S. Pat. No. 3,519,570. A useful Bacillus, sp. AC13 giving proteases, xylanases and cellulases, is described in WO 9401532 A to Novo.

Enzyme Stabilizing System

Enzyme-containing, including but not limited to, liquid compositions, herein may comprise from about 0.001% to about 10%, preferably from about 0.005% to about 8%, most preferably from about 0.01% to about 6%, by weight of an enzyme stabilizing system. The enzyme stabilizing system can be any stabilizing system which is compatible with the detersive enzyme. Such a system may be inherently provided by other formulation actives, or be added separately, e.g., by the formulator or by a manufacturer of detergent-ready enzymes. Such stabilizing systems can, for example, comprise calcium ion, boric acid, propylene glycol, short chain carboxylic acids, boronic acids, and mixtures thereof, and are designed to address different stabilization problems depending on the type and physical form of the detergent composition.

One stabilizing approach is the use of water-soluble sources of calcium and/or magnesium ions in the finished compositions which provide such ions to the enzymes. Calcium ions are generally more effective than magnesium ions and are preferred herein if only one type of cation is being used. Typical detergent compositions, especially liquids, will comprise from about 1 to about 30, preferably from about 2 to about 20, more preferably from about 8 to about 12 millimoles of calcium ion per liter of finished detergent composition, though variation is possible depending on factors including the multiplicity, type and levels of enzymes incorporated. Preferably water-soluble calcium or magnesium salts are employed, including for example calcium chloride, calcium hydroxide, calcium formate, calcium malate, calcium maleate, calcium hydroxide and calcium acetate; more generally, calcium sulfate or magnesium salts corresponding to the exemplified calcium salts may be used. Further increased levels of Calcium and/or Magnesium may of course be useful, for example for promoting the grease-cutting action of certain types of surfactant.

Another stabilizing approach is by use of borate species. See Severson, U.S. Pat. No. 4,537,706. Borate stabilizers, when used, may be at levels of up to 10% or more of the composition though more typically, levels of up to about 3% by weight of boric acid or other borate compounds such as borax or orthoborate are suitable for liquid detergent use. Substituted boric acids such as phenylboronic acid, butane-boronic acid, p-bromophenylboronic acid or the like can be used in place of boric acid and reduced levels of total boron in detergent compositions may be possible though the use of such substituted boron derivatives.

Stabilizing systems of certain cleaning compositions may further comprise from 0 to about 10%, preferably from about 0.01% to about 6% by weight, of chlorine bleach scavengers, added to prevent chlorine bleach species present in many water supplies from attacking and inactivating the enzymes, especially under alkaline conditions. While chlorine levels in water may be small, typically in the range from about 0.5 ppm to about 1.75 ppm, the available chlorine in the total volume of water that comes in contact with the enzyme, for example during fabric- washing, can be relatively large; accordingly, enzyme stability to chlorine in-use is sometimes problematic. Since perborate or percarbonate, which have the ability to react with chlorine bleach, may present in certain of the instant compositions in amounts accounted for separately from the stabilizing system, the use of additional stabilizers against chlorine, may, most generally, not be essential, though improved results may be obtainable from their use. Suitable chlorine scavenger anions are widely known and readily available, and, if used, can be salts containing ammonium cations with sulfite, bisulfite, thiosulfite, thiosulfate, iodide, etc. Antioxidants such as carbamate, ascorbate, etc., organic amines such as ethylenediaminetetracetic acid (EDTA) or alkali metal salt thereof, monoethanolamine (MEA), and mixtures thereof can likewise be used. Likewise, special enzyme inhibition systems can be incorporated such that different enzymes have maximum compatibility. Other conventional scavengers such as bisulfate, nitrate, chloride, sources of hydrogen peroxide such as sodium perborate tetrahydrate, sodium perborate monohydrate and sodium percarbonate, as well as phosphate, condensed phosphate, acetate, benzoate, citrate, formate, lactate, malate, tartrate, salicylate, etc., and mixtures thereof can be used if desired. In general, since the chlorine scavenger function can be performed by ingredients separately listed under better recognized functions, (e.g., hydrogen peroxide sources), there is no absolute requirement to add a separate chlorine scavenger unless a compound performing that function to the desired extent is absent from an enzyme-containing embodiment of the invention; even then, the scavenger is added only for optimum results. Moreover, the formulator will exercise a chemist's normal skill in avoiding the use of any enzyme scavenger or stabilizer which is majorly incompatible, as formulated, with other reactive ingredients, if used. In relation to the use of ammonium salts, such salts can be simply admixed with the detergent composition but are prone to adsorb water and/or liberate ammonia during storage. Accordingly, such materials, if present, are desirably protected in a particle such as that described in U.S. Pat. No. 4,652,392, Baginski et al.

Dispersants

The compositions of the present invention may also optionally comprise at least about 0.1% by weight, preferably from about 0.1% to about 10%, more preferably from about 0.5% to about 5% by weight, of a water-soluble substituted or unsubstituted, modified or urunodified polyalkyleneimine dispersant, said dispersant comprises a polyamine backbone, preferably said backbone having a molecular weight of from about 100 to about 3000 daltons having the formula:

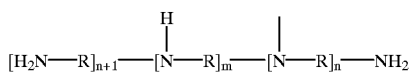

wherein R is preferably $C_2$–$C_6$ alkylene, m is from about 3 to 70, n is from 0 to about 35, one or more of the polyamnine backbone N-H unit hydrogens are "substituted", that is replaced with a substituent which increases the hydrophobic or hydrophilic dispersancy of said polyamine, preferably one or more backbone hydrogens, more preferably all hydrogens are replaced by an propyleneoxy/ethyleneoxy unit having the formula:

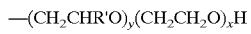

wherein R' is methyl or ethyl, x and y are preferably from about 0 to about 50, provided x+y is at least 1; and wherein further each nitrogen which comprises the polyalkyleneimine backbone may be optionally "modified" by quaternization or by oxidation to the N-oxide.

A flirther description of polyalkyleneimine dispersants is found in U.S. Pat. No. 4,597,898, VanderMeer, issued Jul. 1, 1986; European Patent Application 111,965, Oh and Gosselink, published Jun. 27, 1984; European Patent Application 111,984, Gosselink, published Jun. 27, 1984; European Patent Application 112,592, Gosselink, published Jul. 4, 1984; U.S. Pat. No. 4,548,744, Connor, issued Oct. 22, 1985; and U.S. Pat. No. 5,565,145 Watson et al., issued Oct. 15, 1996; all of which are included herein by reference.

Carriers

The present invention liquid laundry detergent compositons comprises iquid carriers. Sutiable liquid carriers are water, ethanol, methanol, isopropanol, polyethylene glycol, and the like. The preferred carrier of the present invention is water. The water which is used can be distilled, deionized, or tap water.

ADJUNCT INGREDIENTS

The following are non-limiting examples of adjunct ingredients useful in the liquid detergent compositions of the present invention, said adjunct ingredients include builders, optical brighteners, bleach boosters, bleach catalysts, bleach activators, soil release polymers, dye transfer agents, dispersents, enzymes, suds suppressers, dyes, perfiumes, colorants, filler salts, hydrotropes, enzymes, photoactivators, fluorescers, fabric conditioners, hydrolyzable surfactants, preservatives, anti-oxidants, chelants, stabilizers, anti-shrinkage agents, anti-wrinkle agents, germicides, fingicides, anti corrosion agents, and mixtures thereof.

Builders—Detergent builders can optionally be included in the compositions herein to assist in controlling mineral hardness. Inorganic as well as organic builders can be used. Builders are typically used in fabric laundering compositions to assist in the removal of particulate soils.

The level of builder can vary widely depending upon the end use of the composition and its desired physical form. When present, the compositions will typically comprise at least about 1% builder. Formulations typically comprise from about 5% to about 50%, more typically about 5% to about 30%, by weight, of detergent builder.

Inorganic or P-containing detergent builders include, but are not limited to, the alkali metal, amnmonium and alkanolammonium salts of polyphosphates (exemplified by the tripolyphosphates, pyrophosphates, and glassy polymeric meta-phosphates), phosphonates, phytic acid, silicates, carbonates (including bicarbonates and sesquicarbonates), sulphates, and aluminosilicates. For the purposes of the present invention, phosphate builders are one of the preferred builders. However, non-phosphate builders are required in some locales. Importantly, the compositions herein function surprisingly well even in the presence of the so-called "weak" builders (as compared with phosphates) such as citrate, or in the so-called "underbuilt" situation that may occur with zeolite or layered silicate builders.

Examples of silicate builders are the alkali metal silicates, particularly those having a $SiO_2:Na_2O$ ratio in the range 1.6:1 to 3.2:1 and layered silicates, such as the layered sodium silicates described in U.S. Pat. No. 4,66.4,839, issued May 12, 1987 to H. P. Rieck. NaSKS-6 is the trademark for a crystalline layered silicate marketed by Hoechst (commonly abbreviated herein as "SKS-6"). Unlike zeolite builders, the Na SKS-6 silicate builder does not contain aluminum. NaSKS-6 has the delta-$Na_2SiO_5$ morphology form of layered silicate. It can be prepared by methods such as those described in German DE-A-3,417,649 and DE-A-3,742,043. SKS-6 is a highly preferred layered silicate for use herein, but other such layered silicates, such as those having the general formula $NaMSi_xO_{2x+1}·yH_2O$ wherein M is sodium or hydrogen, x is a number from 1.9 to 4, preferably 2, and y is a number from 0 to 20, preferably 0 can be used herein. Various other layered silicates from Hoechst include NaSKS-5, NaSKS-7 and NaSKS- 11, as the alpha, beta and gamma forms. As noted above, the delta-$Na_2SiO_5$ (NaSKS-6 form) is most preferred for use herein. Other silicates may also be useful such as for example magnesium silicate, which can serve as a stabilizing agent for oxygen bleaches, and as a component of suds control systems.

Examples of carbonate builders are the alkaline earth and alkali metal carbonates as disclosed in German Patent Application No. 2,321,001 published on Nov. 15, 1973.

Alumninosilicate builders are useful in the present invention. Aluminosilicate builders can also be a significant builder ingredient in the liquid detergent formulations of the present invention. Aluminosilicate builders include those having the empirical formula:

wherein z and y are integers of at least 6, the molar ratio of z to y is in the range from 1.0 to about 0.5, and x is an integer from about 15 to about 264.

Useful aluminosilicate ion exchange materials are commercially available. These aluminosilicates can be crystalline or amorphous in structure and can be naturally-occurring aluminosilicates or synthetically derived. A method for producing aluminosilicate ion exchange materials is disclosed in U.S. Pat. No. 3,985,669, Krummel, et al, issued Oct. 12, 1976. Preferred synthetic crystalline aluminosilicate ion exchange materials useful herein are available under the designations Zeolite A, Zeolite P(B), Zeolite MAP and Zeolite X. In an especially preferred embodiment, the crystalline aluminosilicate ion exchange material has the formula:

$$Na_{12}[(AlO_2)_{12}(SiO_2)_{12}]\cdot xH_2O$$

wherein x is from about 20 to about 30, especially about 27. This material is known as Zeolite A. Dehydrated zeolites (x=0–10) may also be used herein. Preferably, the aluminosilicate has a particle size of about 0.1–10 microns in diameter.

Organic detergent builders suitable for the purposes of the present invention include, but are not restricted to, a wide variety of polycarboxylate compounds. As used herein, "polycarboxylate" refers to compounds having a plurality of carboxylate groups, preferably at least 3 carboxylates. Polycarboxylate builder can generally be added to the composition in acid form, but can also be added in the form of a neutralized salt. When utilized in salt form, alkali metals, such as sodium, potassium, and lithium, or alkanolammonium salts are preferred.

Included among the polycarboxylate builders are a variety of categories of useful materials. One important category of polycarboxylate builders encompasses the ether polycarboxylates, including oxydisuccinate, as disclosed in Berg, U.S. Pat. No. 3,128,287, issued Apr. 7, 1964, and Lamberti et al, U.S. Pat. No. 3,635,830, issued Jan. 18, 1972. See also "TMS/TDS" builders of U.S. Pat. No. 4,663,071, issued to Bush et al, on May 5, 1987. Suitable ether polycarboxylates also include cyclic compounds, particularly alicyclic compounds, such as those described in U.S. Pat. Nos. 3,923,679; 3,835,163; 4,158,635; 4,120,874 and 4,102,903.

Other useful detergency builders include the ether hydroxypolycarboxylates, copolymers of maleic anhydride with ethylene or vinyl methyl ether, 1,3,5-trihydroxy benzene-2,4,6-trisulphonic acid, and carboxymethyloxysuccinic acid, the various alkali metal, ammonium and substituted ammonium salts of polyacetic acids such as ethylenediamine tetraacetic acid and nitrilotriacetic acid, as well as polycarboxylates such as mellitic acid, succinic acid, oxydisuccinic acid, polymaleic acid, benzene 1,3,5-tricarboxylic acid, carboxymethyloxysuccinic acid, and soluble salts thereof. Citrate builders, e.g., citric acid and soluble salts thereof (particularly sodium salt), are polycarboxylate builders of particular importance for heavy duty liquid detergent formulations due to their availability from renewable resources and their biodegradability.

Also suitable in the detergent compositions of the present invention are the 3,3-dicarboxy-4-oxa-1,6-hexanedioates and the related compounds disclosed in U.S. Pat. No. 4,566,984, Bush, issued Jan. 28, 1986. Useful succinic acid builders include the $C_5$–$C_{20}$ alkyl and alkenyl succinic acids and salts thereof A particularly preferred compound of this type is dodecenylsuccinic acid. Specific examples of succinate builders include: laurylsuccinate, myristylsuccinate, palmitylsuccinate, 2-dodecenylsuccinate (preferred), 2-pentadecenylsuccinate, and the like. Lauiylsuccinates are the preferred builders of this group, and are described in European Patent Application 86200690.5/0,200,263, published Nov. 5, 1986.

Other suitable polycarboxylates are disclosed in U.S. Pat. No. 4,144,226, Crmtchfield et al, issued Mar. 13, 1979 and in U.S. Pat. No. 3,308,067, Diehl, issued Mar. 7, 1967. See also Diehl U.S. Pat. No. 3,723,322.

Fatty acids, e.g., $C_{12}$–$C_{18}$ monocarboxylic acids, can also be incorporated into the compositions alone, or in combination with the aforesaid builders, especially citrate and/or the succinate builders, to provide additional builder activity. Such use of fatty acids will generally result in a diminution of sudsing, which should be taken into account by the formulator.

In situations where phosphorus-based builders can be used, and especially in the formulation of bars used for hand-laundering operations, the various alkali metal phosphates such as the well-known sodium tripolyphosphates, sodium pyrophosphate and sodium orthophosphate can be used. Phosphonate builders such as ethane-1-hydroxy-1,1-diphosphonate and other known phosphonates (see, for example, U.S. Pat. Nos. 3,159,581; 3,213,030; 3,422,021; 3,400,148 and 3,422,137) can also be used.

Soil Release Agents

SRA's suitable for the compositions of the present invention typically have hydrophilic segments to hydrophilize the surface of hydrophobic fibers such as polyester and nylon, and hydrophobic segments to deposit upon hydrophobic fibers and remain adhered thereto through completion of washing and rinsing cycles, thereby serving as an anchor for the hydrophilic segments. This can enable stains occurring subsequent to treatment with the SRA to be more easily cleaned in later washing procedures.

SRA's can include a variety of charged, e.g., anionic or even cationic species, see U.S. Pat. No. 4,956,447, issued Sep. 11, 1990 to Gosselink, et al., as well as noncharged monomer units, and their structures may be linear, branched or even star-shaped. They may include capping moieties which are especially effective in controlling molecular weight or altering the physical or surface-active properties. Structures and charge distributions may be tailored for application to different fiber or textile types and for varied detergent or detergent additive products.

SRA's include oligomeric terephthalate esters, typically prepared by processes involving at least one transesterification/oligomerization, often with a metal catalyst such as a titanium(IV) alkoxide. Such esters may be made using additional monomers capable of being incorporated into the ester structure through one, two, three, four or more positions, without, of course, forming a densely crosslinked overall structure.

Suitable SRA's include a sulfonated product of a substantially linear ester oligomer comprised of an oligomeric ester backbone of terephthaloyl and oxyalkyleneoxy repeat units and allyl-derived sulfonated terminal moieties covalently attached to the backbone, for example as described in U.S. Pat. No. 4,968,451, Nov. 6, 1990 to J. J. Scheibel and E. P. Gosselink. Such ester oligomers can be prepared by: (a) ethoxylating allyl alcohol; (b) reacting the product of (a) with dimethyl terephthalate ("DMT") and 1,2-propylene glycol ("PG") in a two-stage transesterification/oligomerization procedure; and (c) reacting the product of (b) with sodium metabisulfite in water. Other SRA's include the nonionic end-capped 1,2-propylene/polyoxyethylene terephthalate polyesters of U.S. Pat. No. 4,711,730, Dec. 8, 1987 to Gosselink et al., for example those produced by transesterification/-oligomerization of poly(ethyleneglycol) methyl ether, DMT, PG and poly(ethyleneglycol) ("PEG"). Other examples of SRA's include: the partly- and fully- anionic-end-capped oligomeric esters of U.S. Pat. No. 4,721,580, Jan. 26, 1988 to Gosselink, such as oligomers from ethylene glycol ("EG"), PG, DMT and Na-3,6-dioxa-8-hydroxyoctanesulfonate; the nonionic-capped block polyester oligomeric compounds of U.S. Pat. No. 4,702,857, Oct. 27, 1987 to Gosselink, for example produced from DMT, methyl (Me)-capped PEG and EG and/or PG, or a combination of DMT, EG and/or PG, Me-capped PEG and Na-dimethyl-5-sulfoisophthalate; and the anionic, especially sulfoaroyl, end-capped terephthalate esters of U.S. Pat. No. 4,877,896, Oct. 31, 1989 to Maldonado, Gosselink et al., the latter being typical of SRA's useful in both liquid laundry and fabric conditioning products, an example being an ester composition made from m-sulfobenzoic acid monosodium salt, PG and DMT, optionally but preferably fuirther comprising added PEG, e.g., PEG 3400.

SRA's also include: simple copolymeric blocks of ethylene terephthalate or propylene terephthalate with polyethylene oxide or polypropylene oxide terephthalate, see U.S. Pat. No. 3,959,230 to Hays, May 25, 1976 and U.S. Pat. No. 3,893,929 to Basadur, Jul. 8, 1975; cellulosic derivatives such as the hydroxyether cellulosic polymers available as METHOCEL from Dow; the $C_1$–$C_4$ alkyl celluloses and $C_4$ hydroxyalkyl celluloses, see U.S. Pat. No. 4,000,093, Dec. 28, 1976 to Nicol, et al.; and the methyl cellulose ethers having an average degree of substitution (methyl) per anhydroglucose unit from about 1.6 to about 2.3 and a solution viscosity of from about 80 to about 120 centipoise measured at 20° C. as a 2% aqueous solution. Such materials are available as METOLOSE SM100 and METOLOSE SM200, which are the trade names of methyl cellulose ethers manufactured by Shin-etsu Kagaku Kogyo KK.

Suitable SRA's characterised by poly(vinyl ester) hydrophobe segments include graft copolymers of polyvinyl ester), e.g., $C_1$–$C_6$ vinyl esters, preferably poly(vinyl acetate), grafted onto polyalkylene oxide backbones. See European Patent Application 0 219 048, published Apr. 22, 1987 by Kud, et al. Commercially available examples include SOKALAN SRA's such as SOKALAN HP-22, available from BASF, Germany. Other SRA's are polyesters with repeat units containing 10–15% by weight of ethylene terephthalate together with 80–90% by weight of polyoxyethylene terephthalate derived from a polyoxyethylene glycol of average molecular weight 300–5,000. Commercial examples include ZELCON 5126 from Dupont and MILEASE T from ICI.

Additional classes of SRA's include: (I) nonionic terephthalates using diisocyanate coupling agents to link polymeric ester structures, see U.S. Pat. No. 4,201,824, Violland et al. and U.S. Pat. No. 4,240,918 Lagasse et al.; and (II) SRA's with carboxylate terminal groups made by adding trimellitic anhydride to known SRA's to convert terminal hydroxyl groups to trimellitate esters. With the proper selection of catalyst, the trimellitic anhydride forms linkages to the terminals of the polymer through an ester of the isolated carboxylic acid of trimellitic anhydride rather than by opening of the anhydride linkage. Either nonionic or anionic SRA's may be used as starting materials as long as they have hydroxyl terminal groups which may be esterified. See U.S. Pat. No. 4,525,524 Tung et al.. Other classes include: (III) anionic terephthalate-based SRA's of the urethane-linked variety, see U.S. Pat. No. 4,201,824, Violland et al.; (IV) poly(vinyl caprolactam) and related co-polymers with monomers such as vinyl pyrrolidone and/or dimethylaminoethyl methacrylate, including both nonionic and cationic polymers, see U.S. Pat. No. 4,579,681, Ruppert et al.; (V) graft copolymers, in addition to the SOKALAN types from BASF, made by grafting acrylic monomers onto sulfonated polyesters. These SRA's assertedly have soil release and anti-redeposition activity similar to known cellulose ethers: see EP 279,134 A, 1988, to Rhone-Poulenc Chemie. Still other classes include: (VI) grafts of vinyl monomers such as acrylic acid and vinyl acetate onto proteins such as caseins, see EP 457,205 A to BASF (1991); and (VII) polyester-polyamide SRA's prepared by condensing adipic acid, caprolactam, and polyethylene glycol, especially for treating polyamide fabrics, see Bevan et al., DE 2,335,044 to Unilever N. V., 1974. Other useful SRA's are described in U.S. Pat. Nos. 4,240,918, 4,787,989 and 4,525,524.

Other Ingredients—A wide variety of other ingredients useful in detergent compositions can be included in the compositions herein, including other active ingredients, carriers, hydrotropes, processing aids, dyes or pigments, solid fillers for bar compositions, etc. Other optional ingredients include.enzymes, bleaches, bleach activators, bleach catalysts, photoactivators, dyes, fluorescers, fabric conditioners, hydrolyzable surfactants, optical brighteners, preservatives, anti-oxidants, chelants, stabilizers, anti-shrinkage agents, anti-wrinkle agents, soil release agents, germicides, fungicides, and anti corrosion agents. If high sudsing is desired, suds boosters such as the $C_{10}$–$C_{16}$ alkanolamides can be incorporated into the compositions, typically at 1%–10% levels. The $C_{10}$–$C_{14}$ monoethanol and diethanol amides illustrate a typical class of such suds boosters. Use of such suds boosters with high sudsing adjunct surfactants such as the amine oxides, betaines and sultaines noted above is also advantageous. If desired, soluble magnesium salts such as $MgCl_2$, $MgSO_4$, and the like, can be added at levels of, typically, 0.1%–2%, to provide additional suds and to enhance grease removal performance.

Various detersive ingredients employed in the present compositions optionally can be further stabilized by absorbing said ingredients onto a porous hydrophobic substrate, then coating said substrate with a hydrophobic coating. Preferably, the detersive ingredient is admnixed with a surfactant before being absorbed into the porous substrate. In use, the detersive ingredient is released from the substrate into the aqueous washing liquor, where it performs its intended detersive finction.

Method of Use

The present invention also relates to a method for providing enduring fragrance benefits to fabric comprising the step of contacting fabric in an aqueous media with a laundry detergent composition comprising:

a) at least about 0.01%, preferably from about 0.01% to about 15%, more preferably from about 1% to about 5%, most preferably from about 0.1% to about 1% by weight, of a one or more β-ketoester pro-fragrances described herein;

b) at least about 0.01% by weight, preferably from about 0.1% to about 60%, more preferably from about 0.1% to about 30% by weight, of a detersive surfactant selected from the group consisting of anionic, cationic, nonionic, zwitterionic, ampholytic surfactants, and mixtures thereof, preferably said surfactant is an anionic surfactant;

c) at least about 0.001% by weight, of a protease enzyme selected from the group consisting of Protease A, Protease B, Protease D, subtilisin 309 variants, and mixtures thereof; and d) the balance carriers and adjunct ingredients, said adjunct ingredients are selected from the group consisting of builders, optical brighteners, bleaches, bleach boosters, bleach catalysts, bleach activators, soil release polymers, dye transfer agents, dispersants, enzymes, suds suppressers, dyes, perfiunes, colorants, filler salts, hydrotropes, enzymes, photoactivators, fluorescers, fabric conditioners, hydrolyzable surfactants, preservatives, anti-oxidants, chelants, stabilizers, anti-shrinkage agents, anti-wrinkle agents, germicides, fungicides, anti corrosion agents, and mixtures thereof. wherein said laundry composition has a pH of from about 7.2 to about 8.9 when measured as a 10% solution in water.

Non-aqueous compositions

The non-aqueous liquid detergent compositions of the present invention which utilize the β-ketoester fragrance delivery system comprise the following non-limiting ingredients.

Surfactant Containing Liquid Phase

The surfactant-containing, non-aqueous liquid phase will generally comprise from about 49% to about 99.95% by weight of the detergent composition. More preferably, this liquid phase is surfactant structured and will comprise from about 52% to about 98.9% by weight, of the composition. More preferably, this non-aqueous liquid phase will comprise from about 55% to about 70% by weight of the compositions. Typically the surfactant-containing liquid phase has a density of from about 0.6 to 1.4 g/cc, preferably from about 0.9 to 1.3 g/cc. The liquid phase of the detergent compositions are formed from one or more non-aqueous organic diluents into which is admixed a surfactant structuring agent which is preferably a specific type of anionic surfactant-containing powder.

Non-aqueous Organic Diluents

Non-limiting examples of suitable non-aqueous surfactant liquid which can be used to form the liquid phase of the non-aqueous compositions of the present invention include inter alia alkoxylated alcohols, ethylene oxide-propylene oxide block polymers, polyhydroxy fatty acid amides, alkylpolysaccharides. Typically liquid surfactants are those having an HLB ranging from 10 to 16. Preferred surfactant liquids are the alcohol alkoxylate surfactants.

Non-surfactant Non-aqueous Organic Solvents

The liquid phase of the detergent compositions may further comprise one or more non-surfactant, non-aqueous organic solvents. Such non-surfactant non- aqueous liquids are preferably those of low polarity. For the purposes of the present invention, "low polarity" liquids are those which have little, if any, tendency to dissolve one of the preferred types of particulate adjunct ingredients used in the compositions herein. These adjunct ingredients include inter alia peroxygen bleaching agents such as sodium perborate or sodium carbonate. Thus relatively polar solvents such as ethanol are preferably not utilized herein. Suitable solvents of low-polarity useful in the non-aqueous embodiments of the present invention include, but are not limited to, non-vicinal $C_4$–$C_8$ alkylene glycols, alkylene glycol mono lower alkyl ethers, lower molecular weight polyethylene glycols, lower molecular weight methyl ester and amides. Preferred solvents include inter alia hexylene glycol (4-methyl-2,4-pentandiol), 1,6-hexanediol, 1,3-butylene glycol, and 1,4-butylene glycol.

Particulate Materials

Particulate materials suitable for use in the present invention include peroxygen bleaching agents, inorganic builders, sources of alkalinity, chelating agents, and mixtures thereof. Examples of these materials may be found in U.S. Pat. No. 4,483,781 Hartman, issued Nov. 20, 1984; U.S. Pat. No. 4,634,551 Burns et al. issued Jan. 6, 1987 both incorporated herein by reference.

The following examples illustrate the β-keto-esters and compositions of this invention, but are not intended to be limiting thereof.

EXAMPLE 1

Preparation of 3,7-dimethyl-1,6octadien-3-yl 3-(β-naphthyl)-3-oxo-propionate

Lithium diisopropylamnide (101.0 mL of a 2.0 M solution, 0.202 mol) is placed into a 500 mL three-necked round-bottomed flask fitted with a magnetic stirrer, internal thermometer, argon inlet, and addition fiunel. The flask is placed in a dry ice-acetone bath. 3,7-Dimethyl-1,6-octadien-3-yl acetate (linalyl acetate) in the amount of (18.66 g, 0.095 mol) is dissolved in THF (5 mL) and the resulting solution added to the flask over 45 min. Once addition is complete, the mixture is stirred for an additional 15 min before being treated with a solution of 2-naphthoyl chloride in the amount of (17.43 g, 0.090 mol) dissolved in THF (25 mL) over 30 min. The mixture is warmed to −20° C. and stirred at that temperature for 18 h. After warming to 0° C., the mixture is quenched with 20% HCl (53 mL). The mixture is poured into a separatory fumnel containing ether (150 mL) and water (250 mL). The aqueous layer is extracted with ether (150 mL). The combined organic layers are washed with saturated $NaHCO_3$ solution (2×100 mL), water (2×150 mL) and brine (150 mL), dried over $MgSO_4$ and filtered. The solvent is removed by rotary evaporation to give an orange/red oil. The oil is purified by column chromatography (elution with 5% ethyl acetate dissolved in petroleum ether) to give an oil. Purity of the product is determined by thin layer chromatography and GC analysis and the structure confirmed by mass spectrometry, $^1H$ and $^{13}C$ NMR.

EXAMPLE 2

Preparation of 2,6-dimethyl-7-octen-2-yl 3-(4methoxyphenyl)-3-oxo-propionate

N-Isopropylcyclohexylamine (25.00 g, 0.177 mol) and THF in the amount of 200 mL is placed into a 1000 mL three-necked round-bottomed flask fitted with a magnetic stirrer, internal thermometer, argon inlet, and addition fumnel. The flask is placed in a ice-methanol bath cooled to −5° C. and its contents treated with n-butyllithium in the amount of (70.8 mL of a 2.50 M solution, 0.177 mol). The mixture is stirred for 20 min and then cooled to −78° C. 2,6-Dimethyl-7-octen-2-yl acetate (dihydromyrcenyl acetate) in the amount of (17.55 g, 0.089 mol) is dissolved in THF (10 mL) and the resulting solution added to the flask over 45 min. Once addition is complete, the mixture is stirred for an additional 15 min before being treated with a solution of p-methoxybenzoyl chloride in the amount of (15.10 g, 0.090 mol) dissolved in THF (25 ml) over 30 min and then stirred for 1 h. The mixture is warmed to 0° C. and then treated with 90 mL of 20% HCl an hour later. The mixture is poured into a separatory fiunel containing ether (100 ml) and water (200 ml). The aqueous layer is extracted with ether (100 ml). The combined organic layers are washed with saturated $NaHCO_3$ solution (2×100 ml), water (2×100 ml) and brine (100 ml), dried over $MgSO_4$ and filtered. The solvent is removed by rotary evaporation to give an orange/red oil. The oil is purified by column chromatography (elution with 5% ethyl acetate dissolved in petroleum ether) to give an oil. Purity of the product is determined by thin layer chromatography and the structure confirmed by $^1H$ and $^{13}C$ NMR.

EXAMPLE 3

Preparation of 2,6-dimethyl-7-octen-2-yl 3-(4-nitrophenyl) 3-oxo-propionate

Lithium diisopropylamide (121.0 mL of a 2.0 M solution, 0.243 mol) is placed into a 500 mL three-necked round-bottomed flask fitted with a magnetic stirrer, internal thermometer, argon inlet, and addition fimnel. The flask is placed in a dry ice-acetone bath. 2,6-Dimethyl-7-octen-2-yl acetate (22.66 g, 0.114 mol) is dissolved in THF (5 mL) and the resulting solution added to the flask over 45 min. Once addition is complete, the mixture is stirred for an additional 15 min. before being treated with a solution of 4-nitrobenzoyl chloride (20.00 g, 0.108 mol) dissolved in THF (25 niL) over 30 min. The mixture is warmed to −20° C. and stirred at that temperature for 18 h. After warming to 0° C., the mixture is quenched with 20% HCl (70 mL). The mixture is poured into a separatory fumnel containing ether (150 mL) and water (250 mL). The aqueous layer is extracted with ether (150 mL). The combined organic layers are washed with saturated $NaHCO_3$ solution (2×100 mL), water (2×150 mL and brine (150 mL), dried over $MgSO_4$ and filtered. The solvent is removed by rotary evaporation to give an orange/red oil. The oil is purified by column chromatography (elution with 2% ethyl acetate/petroleum ether) to yield a colorless oil having $^1H$ and $^{13}C$ NMR spectra consistent with the desired product.

EXAMPLE 4

Preparation of 2,6-dimethyl-7-octen-2-yl 3-(β-naphthyl)-3-oxo-propionate

Lithium diisopropylamide in the amount of (100.0 mL of a 2.0 M solution, 0.201 mol) is placed into a 500 mL three-necked round-bottomed flask fitted with a magnetic stirrer, internal thermometer, argon inlet, and addition ftnnel. The flask is cooled to −78° C. 2,6-Dimethyl-7-octen-2-yl acetate in the amount of (18.75 g, 0.095 mol) is dissolved in THF (5 mL) and the resulting solution added to the flask over 45 min. Once addition is complete, the mixture is stirred for an additional 15 min before being treated with a solution of 2-naphthoyl chloride in the amount of (17.00 g, 0.089 mol) dissolved in THF (25 mL) over 30 min. The mixture is warmed to −20° C. and stirred at that temperature for 18 h. After warming to 0° C., the mixture is quenched with 20% HCl (55 mL). The mixture is poured into a separatory funnel containing ether (150 mL) and water (250 mL). The aqueous layer is extracted with ether (150 mL). The combined organic layers are washed with saturated $NaHCO_3$ solution (2×100 mL), water (2×150 mL) and brine (150 mL), dried over $MgSO_4$ and filtered. The solvent is removed by rotary evaporation to give an orange/red oil. The oil is purified by column chromatography (elution with 2% ethyl acetate dissolved in petrolewn ether) to give an oil. Purity of the product is determined by thin layer chromatography and the structure confirmed by $^1H$ and $^{13}C$ NMR.

EXAMPLE 5

Preparation of 3.7-dimethyl-1.6-octadien-3-yl 3-methoxyphenyl)3-oxo-propionate

Lithium diisopropylamide (119.0 mL of a 2.0 M solution, 0.238 mol) is placed into a 500 mL three-necked round-bottomed flask fitted with a magnetic stirrer, internal thermometer, argon inlet, and addition fimnel. The flask is cooled to −78° C. 3,7-dimethyl-1,6-octadien-3-yl acetate (22.04 g, 0.112 mol) is dissolved in THF (5 mL) and the resulting solution added to the flask over 45 min. Once addition is complete, the mixture is stirred for an additional 15 min. before being treated with a solution of p-anisoyl chloride (35.00 g, 0.106 mol) dissolved in THF (30 mL) over 30 min. The mixture is warned to −20° C. and stirred at that temperature for 18 h. After warming to 0° C., the mixture is quenched with 20% HCl (80 mL). The mixture is poured into a separatory funnel containing ether (150 mL) and water (250 mL). The aqueous layer is extracted with ether (150 mL). The mixture is poured into a separatory fimnel containing ether (150 mL) and water (250 mL). The aqueous layer is extracted with ether (150 mL). The combined organic layers are washed with saturated $NaHCO_3$ solution (2×100 mL), water (2×150 mL) and brine (150 mL), dried over $MgSO_4$ and filtered. The solvent is removed by rotary evaporation to give an oil. The oil is purified by column chromatography (elution with 2% ethyl acetate/petroleum ether) to yield a colorless oil having $^1H$ and $^{13}C$ NMR spectra consistent with the desired product.

EXAMPLE 6

Preparation of (α,α-4-trimethyl-3-cyclohexenyl)methyl 3-(β-naphthyl)-3-oxo-propionate Lithium diisopropylamide (171.0 mL of a 2.0 M solution, 0.342 mol) is placed into a 1000 mL three-necked round-bottomed flask fitted with a magnetic stirrer, internal thermometer, argon inlet, and addition fimnel. The flask is cooled to −78° C. (α,α-4-Trimethyl-3-cyclohexenyl)methyl acetate (30.00 g, 0.153 mol) is dissolved in THF (10 mL) and the resulting solution added to the flask over 45 min. Once addition is complete, the mixture is stirred for an additional 15 min. before being treated with a solution of 2-naphthoyl chloride (29.00 g, 0.152 mol) dissolved in THF (50 mL) over 30 min. The mixture is warmed to −20° C. and stirred at that temperature for 18 h. After warming to 0° C., the mixture is quenched with 20% HCl (105 mL). The mixture is poured into a separatory funnel containing ether (150 mL) and water (250 mL). The mixture is poured into a separatory fimnel containing ether (150 mL) and water (250 mL). The aqueous layer is extracted with ether (150 mL). The combined organic layers are washed with saturated $NaHCO_3$ solution (2×100 mL), water (2×150 mL) and brine (150 mL), dried over $MgSO_4$ and filtered. The solvent is removed by rotary evaporation to give an oil. The oil is purified by column chromatography (elution with 2% ethyl acetate/petroleum ether) to yield a semi-white solid which is triturated in cold n-pentane to yield a white powder having $^1H$ and $^{13}C$ NMR spectra consistent with the desired product..

EXAMPLE 7

Preparation of 3,7-dimethyl-1.6-octadien-3-yl 3-(a-naphthyl)-3-oxo-propionate

Lithium diisopropylamide (96.3 mL of a 2.0 M solution, 0.193 mol) is placed into a 500 mL three-necked round-bottomed flask fitted with a magnetic stirrer, internal thermometer, argon inlet, and addition fimnel. The flask is cooled to −78° C. 3,7-dimethyl-1,6-octadien-3-yl acetate (17.81 g, 0.091 mol) is dissolved in THF (5 mL) and the resulting solution added to the flask over 45 min. Once addition is complete, the mixture is stirred for an additional 15 min. before being treated with a solution of 1-naphthoyl chloride (16.82 g, 0.086 mol) dissolved in THF (25 mL) over 30 min. The mixture is warned to −20° C. and stirred at that temperature for 18 h. After warming to 0° C., the mixture is quenched with 20% HCl (53 mL). The mixture is poured into a separatory fimnel containing ether (150 mL) and water (250 mL). The aqueous layer is extracted with ether (150 mL). The combined organic layers are washed with saturated $NaHCO_3$ solution (2×100 mL), water (2×150 mL) and brine (150 mL), dried over $MgSO_4$ and filtered. The solvent is removed by rotary evaporation to give an oil. The oil is purfied by column chromatography (elution with 2% ethyl acetate/petroleum ether) to yield a colorless oil having 1H and $^{13}C$ NMR spectra consistent with the desired product.

EXAMPLE 8

Preparation of cis 3-hexen-1-yl 3-(β-naphthyl)-3-oxo-propionate

Lithium diisopropylamide (133.0 mL of a 2.0 M solution, 0.266 mol) is placed into a 500 mL three-necked round-bottomed flask fitted with a magnetic stirrer, internal thermometer, argon inlet, and addition funnel. The flask is cooled to −78° C. cis 3-Hexenyl acetate (17.80 g, 0.125 mol) is dissolved in THF (10 mL) and the resulting solution added to the flask over 45 min. Once addition is complete, the mixture is stirred for an additional 15 min. before being treated with a solution of 2-naphthoyl chloride (22.51 g, 0.118 mol) dissolved in THF (30 mL) over 30 min. The mixture is warmed to −20° C. and stirred at that temperature for 18 h. After warming to 0° C., the mixture is quenched with 20% HCl (70 mL). The mixture is poured into a separatory fimnel containing ether (150 mL) and water (250 mL). The aqueous layer is extracted with ether (150 mL). The combined organic layers are washed with saturated NaHCO$_3$ solution (2×100 mL), water (2×150 mL) and brine (150 mL), dried over MgSO$_4$ and filtered. The solvent is removed by rotary evaporation to give an orange/red oil. The oil is purified by column chromatography (elution with 2% ethyl acetate/petroleum ether) to yield a colorless oil having $^1$H and $^{13}$C NMR spectra consistent with the desired product.

EXAMPLE 9

Preparation of 9decen-1-yl 3-(β-naphthyl)-3-oxo-propionate

Lithium diisopropylamide (79.8 mL of a 2.0 M solution, 0.160 mol) is placed into a 250 mL three-necked round-bottomed flask fitted with a magnetic stirrer, internal thermometer, argon inlet, and addition fimnel. The flask is cooled to −78° C. 9-Decen-1-yl acetate (14.91 g, 0.075 mol) is dissolved in THF (5 mL) and the resulting solution added to the flask over 45 min. Once addition is complete, the mixture is stirred for an additional 15 min. before being treated with a solution of 2-naphthoyl chloride (13.80 g, 0.071 mol) dissolved in THF (25 mL) over 30 min. The mixture is warmed to −20° C. and stirred at that temperature for 18 h. After warming to 0° C., the mixture is quenched with 20% HCl (47 mL). The mixture is poured into a separatory fimnel containing ether (150 mL) and water (250 mL). The aqueous layer is extracted with ether (150 mL). The combined organic layers are washed with saturated NaHCO$_3$ solution (2×100 mL), water (2×150 mL) and brine (150 mL), dried over MgSO$_4$ and filtered. The solvent is removed by rotary evaporation to give an orange/red oil. The oil is purified by column chromatography (elution with 2% ethyl acetate/petroleum ether) to yield a colorless oil having $^1$H and $^{13}$C NMR spectra consistent with the desired product.

EXAMPLE 10

Preparation of 3,7-dimethyl-1,6octadien-3-yl 3(nonanyl)-3-oxo-propionate

Lithium diisopropylamide (133.7 mL of a 2.0 M solution, 0.267 mol) is placed into a 500 mL three-necked round-bottomed flask fitted with a magnetic stirrer, internal thermometer, argon inlet, and addition fimnel. The flask is cooled to −78° C. 3,7-dimethyl-1,6octadien-3-yl acetate (24.73 g, 0.126 mol) is dissolved in THF (40 mL) and the resulting solution added to the flask over 45 min. Once addition is complete, the mixture is stirred for an additional 15 min. before being treated with a solution of nonanoyl chloride (21.88 g, 0.119 mol) over 30 min. The mixture is warmed to −20° C. and stirred at that temperature for 18 h. After warming to 0° C., the mixture is quenched with 20% HCl (60 mL). The mixture is poured into a separatory finnel containing ether (150 mL) and water (250 mL). The aqueous layer is extracted with ether (150 mL). The combined organic layers are washed with saturated NaHCO$_3$ solution (2×100 mL), water (2×150 mL) and brine (150 mL), dried over MgSO$_4$ and filtered. The solvent is removed by rotary evaporation to give an orangelred oil. The oil is purified by column chromatography (elution with 2% ethyl acetate/petroleum ether) to yield a colorless oil having $^1$H and $^{13}$C NMR spectra consistent with the desired product.

EXAMPLE 11

Preparation of 2,6-dimethyl-7-octen-2-yl 3-(nonanyl)-3-oxo-propionate

Lithium diisopropylamide (75.7 mL of a 2.0 M solution, 0.151 mol) is placed into a 500 mL three-necked round-bottomed flask fitted with a magnetic stirrer, internal thermometer, argon inlet, and addition funnel. The flask is cooled to −78° C. 2,6-Dimethyl-7octen-2-yl acetate (14.14 g, 0.071 mol) is dissolved in THF (20 mL) and the resulting solution added to the flask over 45 min. Once addition is complete, the mixture is stirred for an additional 15 min. before being treated with a solution of nonanoyl chloride (12.38 g, 0.067 mol) over 30 min. The mixture is warmed to −20° C. and stirred at that temperature for 18 h. After warming to 0° C., the mixture is quenched with 20% HCl (55 mL). The mixture is poured into a separatory funnel containing ether (150 mL) and water (250 mL). The aqueous layer is extracted with ether (150 mL). The combined organic layers are washed with saturated NaHCO$_3$ solution (2×100 mL), water (2×150 mL) and brine (150 mL), dried over MgSO$_4$ and filtered. The solvent is removed by rotary evaporation to give an orange/red oil. The oil is purified by column chromatography (elution with 2% ethyl acetate/petroleum ether) to yield a colorless oil having $^1$H and $^{13}$C NMR spectra consistent with the desired product.

EXAMPLE 12

Preparation of 3,7-dimethyl-1,6octadien-3-yl 3-oxo-butyrate

A mixture of linalool (100 g, 0.648 mol) and 4-dimethylaminopyridine (0.40 g, 3.20 mmol) in a 500 mL three-necked round-bottomed flask fitted with a condenser, argon inlet, addition fiunel, magnetic stirrer and internal thermometer is heated to 55° C. Diketene (54.50 g, 0.648 mol) is added dropwise in the course of 30 min. The mixture has a slight exotherm and turns from yellow to red during this time. After stirring an additional hour at 50° C., the mixture is cooled to room temperature. At this point, NMR analysis indicates the reaction is complete. The material from this lot is carried onto the next step. Purification of an earlier sample from this route by flash chromatography (elution with dichloromethane) yields the desired product in 92% yield and nearly colorless.

EXAMPLE 13

Preparation of 2,6-dimethyl-7-octen-2-yl 3-oxo-butyrate

A mixture of dihydromyrcenol (37.88 g, 0.240 mol) and 4-dimethylarninopyridine (0.16 g, 1.30 mmol) in a 100 mL three-necked round-bottomed flask fitted with a condenser, argon inlet, addition funnel, magnetic stirrer and internal thermometer is heated to 50–60° C. Diketene (20.16 g, 0 . . . 240 mol) is added dropwise in the course of 15 min. The mixture has a slight exotherm and turned from yellow to red during this time. After stirring an additional hour at 50° C., the mixture is cooled to room temperature. At this point, NMR analysis indicates the reaction is complete. Purification of the product mixture by flash chromatography (elution with dichloromethane) yields the desired product in 95% yield as a nearly colorless oil.

EXAMPLE 14
Preparation of 3,7-dimethyl-1,6octadien-3-yl 3-(β-naphthyl)-3-oxo-propionate Crude 3,7-dimethyl-1,6-octadien-3-yl 3-oxo-butyrate (154.51, 0.648 mol) from above is placed in a 3000 mL three-necked round-bottomed flask fitted with a condenser, argon inlet, addition funnel, magnetic stirrer and internal thermometer. The contents are dissolved in 350 mL of dichloromethane and treated with powdered calcium hydroxide (50.44 g, 0.681 mol). The mixture is stirred at 30° C. for 30 min and then heated to 40° C. 2-Naphthoyl chloride (142.12 g, 0.746 mol) dissolved in 20 mL of dichloromethane is added dropwise over 15 min. The mixture continues to be heated at this temperature for 1 h. Ammonium chloride (36.41 g, 0.681 mol) dissolved in 250 mL of water is added to the reaction mixture and the pH adjusted to ~9 with 28% ammonium hydroxide. After stirring 30 min at 35° C. the pH is adjusted to ~1 with 20% HCl. The mixture is transferred to a separatory funnel containing diethyl ether (500 mL) and water (500 mL). The layers are separated and the organic phase is washed with saturated $NaHCO_3$ solution (2×500 mL), dried over $MgSO_4$, filtered and concentrated by rotary evaporation to give a yellow red oil. At this point a light yellow solid precipitates from the mixture. An equal volume of hexane is added and the solids is collected by filtration and dried. NMR analysis indicates the solid is 2-naphthoic acid. The eluent is concentrated again by rotary evaporation to give a red oil. The oil is taken up in an equal volume of dichloromethane, passed through a plug of silica gel (400 g) and eluted with dichloromethane. The mixture is concentrated by rotary evaporation and stripped by Kugelrohr distillation (40° C., 0.10 mm Hg, 30 min) to yield 173.26 g (76.3%) of the product as a red oil; this product is a mixture of a 1:10 molar ratio of linalyl acetoacetate to linalyl (2-naphthoylacetate. A portion of this material is purified by column chromatography (elution with 2.5% ethyl acetate in hexanes) to give the desired product as a light yellow oil.

EXAMPLE 15
Preparation of 3,7-dimethyl-1,6octadien-3-yl 3-(β-naphthyl)-3-oxo-2,2-dimethylpropionate Sodium hydride (2.30 g, 0.057 mol, 60%) and tetrahydrofuran (50 mL) are placed into a 250 mL three-necked round-bottomed flask fitted with a magnetic stirrer, ice bath, addition fimnel, internal thermometer and argon inlet. The contents of the flask are cooled to 0° C. 3,7-Dimethyl-1,6-octadien-3-yl 3-(β-naphthyl)-3-oxo-propionate (8.94 g, 0.025 mol) dissolved in 50 mL of tetrahydrofi=ran is added dropwise to the flask over 30 min. During addition, the mixture evolves gas. After stirring for 1 h, methyl iodide (7.24 g, 0.051 mol) is added to the reaction mixture. Stirring continues for 2 h at 0° C. and then at room temperature for 18 h. The mixture is neutralized with 20% HCl and extracted with diethyl ether. The organic layers are washed with saturated $NaHCO_3$ solution, water, dried over $MgSO_4$, filtered, concentrated by rotary evaporation and purified by flash chromatography to yield the desired compound. Structure is confirmed my $^1H$ and $^{13}C$ NMR.

EXAMPLE 16
Preparation of 3,7-dimethyl-1,6-octadien-3-yl 3(β-naphthyl)-3-oxo-2-methylpropionate Sodium hydride (3.92 g, 0.098 mol, 60%) and tetrahydrofuran (100 mL) are placed into a 250 mL three-necked round-bottomed flask fitted with a magnetic stirrer, ice bath, addition funnel, internal thermometer and argon inlet. The contents of the flask are cooled to 0° C. 3,7-Dimethyl-1,6-octadien-3-yl 3-(β-naphthyl)-3-oxo-propionate (15.28 g, 0.044 mol) dissolved in 50 mL of tetrahydrofuran is added dropwise to the flask over 30 min. During addition, the mixture evolves gas. After stirring for 1 h, methyl iodide (10.65 g, 0.075 mol) is added to the reaction mixture. Stirring continues for 2 h at 0° C. and then at room temperature for 18 h. The mixture is neutralized with 20% HCl and extracted with diethyl ether. The organic layers are washed with saturated $NaHCO_3$ solution, water, dried over $MgSO_4$, filtered, concentrated by rotary evaporation and purified by flash chromatography to yield the desired compound. Structure is confirmed my $^1H$ and $^{13}C$ NMR.

EXAMPLE 17
Preparation of 3,7-dimethyl-1,6-octadien-3-yl 3-(hexyl)-3-oxo-propionate 3,7-Dimethyl-1,6-octadien-3-yl 3-oxo-butyrate (30.00 g, 0.126 mol), dichloromethane (50 mL) and methyl ethyl ketone (10 mL) are combined in a 500 mL three-necked round-bottomed flask fitted with an internal thermometer, addition funnel, condenser and argon inlet. Calcium hydroxide (9.80 g, 0.132 mol, powdered) is added to the flask and the slurry stirs for 1 h. Heptanoyl chloride (17.84 g, 0.120 mol) in 10 ml of dichloromethane is added over 15 min so as to keep the reaction temperature between 35–40° C. The reaction continues to stir at 35–40° C. for 2 h. Ammonium chloride (7.06 g, 0.132 mol) dissolved in 20 mL of water is added to the flask. After 20 min, concentrated ammonium hydroxide is added to the mixture to adjust the pH to ~9.0. After 1 h, 20% HCl solution is added to drop the pH to ~1.0. After 1 h, the mixture is poured into 300 mL of dichloromethane. The layers are separated and the aqueous phase extracted with 100 mL of dichloromethane. The combine organic layers are washed with saturated $NaHCO_3$ solution, water, dried over $MgSO_4$, filtered, concentrated by rotary evaporation and purified by flash chromatography to yield the desired compound. Structure is confirmed my $^1H$ and $^{13}C$ NMR.

EXAMPLE 18
Preparation of 3,7-dimethyl-1,6-octadien-3-yl 3-oxo-2-benzylbutyrate Potassium carbonate (3.92 g, 0.028 mol), 3,7-dimethyl-1,6-octadien-3-yl 3-oxo-butyrate (4.80 g, 0.030 mol), benzyl chloride (4.80 g, 0.038 mol) and acetone (15 mL) are placed in a 50 mL round-bottomed flask fitted with a magnetic stirrer, condenser and argon inlet. The mixture is heated to reflux for 18 h. The cooled mixture is filtered and concentrated by rotary evaporation. The resulting oil is purified on silica gel to yield the desired compound. Structure is confirmed by thin layer chromatography and $^1H$ and $^{13}C$ NMR.

The following describe heavy duty liquid detergent compositions according to the present invention:

TABLE I

| | weight % | | | |
|---|---|---|---|---|
| Ingredient | 19 | 20 | 21 | 22 |
| Polyhydroxy Coco-Fatty Acid Amide | 2.50 | 2.50 | — | — |
| $C_{12}$–$C_{13}$ Alcohol Ethoxylate $E_o$ | — | — | 3.65 | 0.80 |
| Sodium $C_{12}$–$C_{15}$ Alcohol Sulfate | — | — | 6.03 | 2.50 |
| Sodium $C_{12}$–$C_{15}$ Alcohol Ethoxylate $E_{1.8}$ Sulfate | 20.15 | 20.15 | — | — |

TABLE I-continued

| Ingredient | weight % | | | |
|---|---|---|---|---|
| | 19 | 20 | 21 | 22 |
| Sodium $C_{14}$–$C_{15}$ Alcohol Ethoxylate $E_{2.25}$ Sulfate | — | — | 18.00 | 18.00 |
| Alkyl N-Methyl Glucose Amide | — | — | 4.50 | 4.50 |
| $C_{10}$ Amidopropyl Amine | 0.50 | 0.50 | 1.30 | — |
| Citric Acid | 2.44 | 3.00 | 3.00 | 3.00 |
| Fatty Acid ($C_{12}$–$C_{14}$) | — | — | 2.00 | 2.00 |
| NEODOL 23-9[1] | 0.63 | 0.63 | — | — |
| Ethanol | 3.00 | 2.81 | 3.40 | 3.40 |
| Monoethanolamine | 1.50 | 0.75 | 1.00 | 1.00 |
| Propanediol | 8.00 | 7.50 | 7.50 | 7.00 |
| Boric Acid | 3.50 | 3.50 | 3.50 | 3.50 |
| Ethoxylated tetraethylene-pentamine[2] | 0.50 | — | — | — |
| Tetraethylenepentamine | — | 1.18 | — | — |
| Sodium Toluene Sulfonate | 2.50 | 2.25 | 2.50 | 2.50 |
| NaOH | 2.08 | 2.43 | 2.62 | 2.62 |
| Protease enzyme[3] | 0.78 | 0.70 | — | — |
| Protease enzyme[4] | — | — | 0.88 | — |
| ALCALASE[5] | — | — | — | 1.00 |
| Dispersant[6] | 0.50 | 0.50 | 2.00 | 1.00 |
| Pro-fragrance[7] | 1.00 | 1.25 | 1.50 | 2.00 |
| Water[8] | balance | balance | balance | balance |

[1]$E_9$ Ethoxylated Alcohols as sold by the Shell Oil Co.
[2]Ethoxylated tetraethylenepentamine (PEI 189 $E_{15}$–$E_{18}$) according to U.S. Pat. No. 4,597,898 Vander Meer issued July 1, 1986.
[3]Bleach stable variant of BPN' (Protease A-BSV) as disclosed in EP 130, 756 A January 9, 1985.
[4]Subtilisin 309 Loop Region 6 variant.
[5]Proteolytic enzyme as sold by Novo.
[6]PEI 1800 $E_7$ according to U.S. Pat. No. 5,565,145 Watson et al., issued October 15, 1996.
[7]Pro-fragrance according to Example 1.
[8]Balance to 100% can, for example, include minors like optical brightener, perfume, suds suppresser, soil dispersant, chelating agents, dye transfer inhibiting agents, additional water, and fillers, including $CaCO_3$, talc, silicates, etc.

TABLE II

| Ingredient | weight % | | | |
|---|---|---|---|---|
| | 23 | 24 | 25 | 26 |
| Polyhydroxy Coco-Fatty Acid Amide | 3.65 | 3.50 | — | — |
| $C_{12}$–$C_{13}$ Alcohol Ethoxylate $E_9$ | 3.65 | 0.80 | — | — |
| Sodium $C_{12}$–$C_{15}$ Alcohol Sulfate | 6.03 | 2.56 | — | — |
| Sodium $C_{12}$–$C_{15}$ Alcohol Ethoxylate $E_{2.5}$ Sulfate | 9.29 | 15.10 | — | — |
| Sodium $C_{14}$–$C_{15}$ Alcohol Ethoxylate $E_{2.25}$ Sulfate | — | — | 18.00 | 18.00 |
| Alkyl N-Methyl Glucose Amide | — | — | 4.50 | 4.50 |
| $C_{10}$ Amidopropyl Amine | — | 1.30 | — | — |
| Citric Acid | 2.44 | 3.00 | 3.00 | 3.00 |
| Fatty Acid ($C_{12}$–$C_{14}$) | 4.23 | 2.00 | 2.00 | 2.00 |
| NEODOL 23-9[1] | — | — | 2.00 | 2.00 |
| Ethanol | 3.00 | 2.81 | 3.40 | 3.40 |
| Monoethanolamine | 1.50 | 0.75 | 1.00 | 1.00 |
| Propanediol | 8.00 | 7.50 | 7.50 | 7.00 |
| Boric Acid | 3.50 | 3.50 | 3.50 | 3.50 |
| Tetraethylenepentamine | — | 1.18 | — | — |
| Sodium Toluene Sulfonate | 2.50 | 2.25 | 2.50 | 2.50 |
| NaOH | 2.08 | 2.43 | 2.62 | 2.62 |
| Protease enzyme[2] | 0.78 | 0.70 | — | — |
| Protease enzyme[3] | — | — | 0.88 | — |
| ALCALASE[4] | — | — | — | 1.00 |
| Dispersant[5] | 0.50 | 0.50 | 2.00 | 1.00 |
| Pro-fragrance[6] | 2.00 | 1.50 | 1.50 | 2.50 |
| Water[7] | balance | balance | balance | balance |

[1]$E_9$ Ethoxylated Alcohols as sold by the Shell Oil Co.
[2]Bleach stable variant of BPN' (Protease A-BSV) as disclosed in EP 130, 756 A January 9, 1985.
[3]Subtilisin 309 Loop Region 6 variant.
[4]Proteolytic enzyme as sold by Novo.
[5]PEI 1200 $E_7$ according to U.S. Pat. No. 5,565,145 Watson et al., issued October 15, 1996.
[6]Cotton soil release polymer according to Example 7 (PEI 600 E20).
[7]Pro-fragrance according to Example 4.
[8]Balance to 100% can, for example, include minors like optical brightener, perfume, suds suppresser, soil dispersant, chelating agents, dye transfer inhibiting agents, additional water, and fillers, including $CaCO_3$, talc, silicates, etc.

TABLE III

| Ingredient | 27 | 28 | 29 | 30 |
|---|---|---|---|---|
| Sodium $C_{14}$–$C_{15}$ Alcohol Ethoxylate $E_{2.25}$ Sulfate | 13.00 | — | — | 8.43 |
| Sodium $C_{12}$–$C_{15}$ Alcohol Ethoxylate $E_{2.5}$ Sulfate | — | 18.00 | 13.00 | — |
| Sodium $C_{12}$–$C_{13}$ linear alkyl-benzene sulfonate | 9.86 | — | — | 8.43 |
| Fatty Acid ($C_{12}$–$C_{14}$) | — | 2.00 | 2.00 | 2.95 |
| $C_{12}$–$C_{13}$ Alcohol Ethoxylate $E_9$ | — | — | — | 3.37 |
| $C_{10}$ Amidopropyl Amine | — | — | 0.80 | — |
| NEODOL 23-9[1] | 2.22 | 2.00 | 1.60 | — |
| Alkyl N-Methyl Glucose Amide | — | 5.00 | 2.50 | — |
| Citric Acid | 7.10 | 3.00 | 3.00 | 3.37 |
| Ethanol | 1.92 | 3.52 | 3.41 | 1.47 |
| Monoethanolamine | 0.71 | 1.09 | 1.00 | 1.05 |
| Propanediol | 4.86 | 8.00 | 6.51 | 6.00 |
| Boric Acid | 2.22 | 3.30 | 2.50 | — |
| Ethoxylated Tetraethylene-pentamine | 1.18 | 1.18 | — | 1.48 |
| Sodium Cumene Sulfonate | 1.80 | 3.00 | — | 3.00 |
| Sodium Toluene Sulfonate | — | — | 2.50 | — |
| NaOH | 6.60 | 2.82 | 2.90 | 2.10 |
| Dodecyltrimethylammonium Chloride | — | — | — | 0.51 |
| Sodium Tartrate Mono and Di-succinate | — | — | — | 3.37 |
| Sodium Formate | — | — | — | 0.32 |
| Protease D[2] | 0.88 | 0.88 | — | — |
| Protease subtilisin 309 variant[3] | — | — | 0.78 | 0.56 |
| Dispersant[4] | 0.50 | 2.00 | 2.00 | 3.00 |
| Pro-perfume[5] | 1.00 | 1.00 | 1.25 | 1.50 |
| Water[6] | balance | balance | balance | balance |

[1]$E_9$ Ethoxylated Alcohols as sold by the Shell Oil Co.
[2]Protease B variant of BPN' wherein Tyr 217 is replaced with Leu.
[3]Subtilisin 309 variant having a modified amino acid sequence of subtilisin 309 wild-type amino acid sequence wherein substitutions occur at one or more of positions 194, 195, 196, 199 or 200.
[4]PEI 1800 $E_7$ according to U.S. Pat. No. 5,565,145 Watson et al., issued October 15, 1996.
[5]Pro-perfume according to Example 6.
[6]Balance to 100% can, for example, include minors like optical brightener, perfume, suds suppresser, soil dispersant, chelating agents, dye transfer inhibiting agents, additional water, and fillers, including $CaCO_3$, talc, silicates, etc.

TABLE IV

| Ingredient | 31 | 32 | 33 | 34 |
|---|---|---|---|---|
| Sodium $C_{14}$–$C_{15}$ Alcohol Ethoxylate $E_{2.25}$ Sulfate | 13.00 | — | — | 8.43 |

TABLE IV-continued

| Ingredient | 31 | 32 | 33 | 34 |
|---|---|---|---|---|
| Sodium $C_{12}$–$C_{15}$ Alcohol Ethoxylate $E_{2.5}$ Sulfate | — | 18.00 | 13.00 | — |
| Sodium $C_{12}$–$C_{13}$ linear alkylbenzene sulfonate | 9.86 | — | — | 8.43 |
| Fatty Acid ($C_{12}$–$C_{14}$) | — | 2.00 | 2.00 | 2.95 |
| $C_{12}$–$C_{13}$ Alcohol Ethoxylate $E_9$ | — | — | — | 3.37 |
| $C_{10}$ Amidopropyl Amine | — | — | 0.80 | — |
| NEODOL 23-9[1] | 2.22 | 2.00 | 1.60 | — |
| Alkyl N-Methyl Glucose Amide | — | 5.00 | 2.50 | — |
| Citric Acid | 7.10 | 3.00 | 3.00 | 3.37 |
| Ethanol | 1.92 | 3.52 | 3.41 | 1.47 |
| Monoethanolamine | 0.71 | 1.09 | 1.00 | 1.05 |
| Propanediol | 4.86 | 8.00 | 6.51 | 6.00 |
| Boric Acid | 2.22 | 3.30 | 2.50 | — |
| Ethoxylated Tetraethylenepentamine | 1.18 | 1.18 | — | 1.48 |
| Sodium Cumene Sulfonate | 1.80 | 3.00 | — | 3.00 |
| Sodium Toluene Sulfonate | — | — | 2.50 | — |
| NaOH | 6.60 | 2.82 | 2.90 | 2.10 |
| Dodecyltrimethylammonium Chloride | — | — | — | 0.51 |
| Sodium Tartrate Mono and Di-succinate | — | — | — | 3.37 |
| Sodium Formate | — | — | — | 0.32 |
| Protease D[2] | 0.88 | 0.88 | — | — |
| Protease subtilisin 309 variant[3] | — | — | 0.78 | 0.56 |
| Dispersant[4] | 0.50 | 2.00 | 2.00 | 3.00 |
| Pro-fragrance[5] | 1.50 | 2.00 | 2.00 | 2.50 |
| Water[6] | balance | balance | balance | balance |

[1] $E_9$ Ethoxylated Alcohols as sold by the Shell Oil Co.
[2] Protease B variant of BPN' wherein Tyr 217 is replaced with Leu.
[3] Subtilisin 309 variant having a modified amino acid sequence of subtilisin 309 wild-type amino acid sequence wherein substitutions occur at one or more of positions 194, 195, 196, 199 or 200.
[4] PEI 189 $E_{15}$–$E_{18}$ according to U.S. Pat. No. 4,597,898 Vander Meer issued July 1, 1986.
[5] Pro-fragrance according to Example 12.
[6] Balance to 100% can, for example, include minors like optical brightener, perfume, suds suppresser, soil dispersant, chelating agents, dye transfer inhibiting agents, additional water, and fillers, including $CaCO_3$, talc, silicates, etc.

TABLE V

| Ingredients | 35 | 36 | 37 | 38 | 39 |
|---|---|---|---|---|---|
| Polyhydroxy coco-fatty acid amide | 3.50 | 3.50 | 3.15 | 3.50 | 3.00 |
| NEODOL 23-9[1] | 2.00 | 0.60 | 2.00 | 0.60 | 0.60 |
| $C_{25}$ Alkyl ethoxylate sulphate | 19.00 | 19.40 | 19.00 | 17.40 | 14.00 |
| $C_{25}$ Alkyl sulfate | — | — | — | 2.85 | 2.30 |
| $C_{10}$-Aminopropylamide | — | — | — | 0.75 | 0.50 |
| Citric acid | 3.00 | 3.00 | 3.00 | 3.00 | 3.00 |
| Tallow fatty acid | 2.00 | 2.00 | 2.00 | 2.00 | 2.00 |
| Ethanol | 3.41 | 3.47 | 3.34 | 3.59 | 2.93 |
| Propanediol | 6.22 | 6.35 | 6.21 | 6.56 | 5.75 |
| Monomethanol amine | 1.00 | 0.50 | 0.50 | 0.50 | 0.50 |
| Sodium hydroxide | 3.05 | 2.40 | 2.40 | 2.40 | 2.40 |
| Sodium p-toluene sulfonate | 2.50 | 2.25 | 2.25 | 2.25 | 2.25 |
| Borax | 2.50 | 2.50 | 2.50 | 2.50 | 2.50 |
| Protease[2] | 0.88 | 0.88 | 0.88 | 0.88 | 0.88 |
| Lipolase[3] | 0.04 | 0.12 | 0.12 | 0.12 | 0.12 |
| Duramyl[4] | 0.10 | 0.10 | 0.10 | 0.10 | 0.40 |
| CAREZYME | 0.053 | 0.053 | 0.053 | 0.053 | 0.053 |
| Optical Brightener | 0.15 | 0.15 | 0.15 | 0.15 | 0.15 |
| Pro-fragrance[5] | — | 1.25 | 1.50 | — | 1.50 |
| Pro-fragrance[6] | 1.00 | — | — | 1.50 | — |
| Fumed silica | 0.119 | 0.119 | 0.119 | 0.119 | 0.119 |
| Minors, aestetics, water | balance | balance | balance | balance | balance |

[1] $C_{12}$–$C_{13}$ alkyl $E_9$ ethoxylate as sold by Shell Oil Co.
[2] Bacillus amyloliquefaciens subtilisin as described in WO 95/10615 published April 20, 1995 by Genencor International.
[3] Derived from Humicola lanuginosa and commercially available from Novo.
[4] Disclosed in WO 9510603 A and available from Novo.
[5] Pro-fragrance according to Example 13.
[6] Pro-fragrance according to Example 6.

The following are examples of non-aqueous detergent compositions according to the present invention.

TABLE VI

| | weight % | |
|---|---|---|
| Ingredients | 40 | 41 |
| Sodium $C_{12}$–$C_{13}$ linear alkylbenzene sulfonate | 16.0 | 16.0 |
| $C_{12}$–$C_{14}$ Alcohol Ethoxylate $E_5$ | 22.0 | 22.0 |
| Butoxy Propoxy Propanol | 19.0 | 19.0 |
| Sodium citrate dihydrate | 3.0 | 3.0 |
| Bleach activator | 5.9 | 5.9 |
| Sodium carbonate | 9.0 | 9.0 |
| Maleic-acrylic co-polymer | 3.0 | 3.0 |
| Ethylenediamine-N,N'-disuccinnic acid | 1.0 | 1.0 |
| Cellulase prills | 0.12 | 0.12 |
| Amylase prills | 0.4 | 0.4 |
| Quaternized ethoxylated hexylenediamine[1] | 1.25 | 1.25 |
| Sodium perborate | 15.0 | 15.0 |
| Thickener | 0.4 | 0.4 |
| Suds suppressor | 0.04 | 0.04 |
| Pro-fragrance[2] | 0.48 | — |
| Pro-fragrance[3] | — | 0.56 |
| Titanium dioxide | 0.5 | 0.5 |
| Optical brightener | 0.2 | 0.2 |
| Sulfate | 2.31 | 2.23 |
| Total | 100.00 | 100.00 |

[1] Dispersent according to U.S. Pat. No. 4,548,744 Connor, issued October 22, 1985.
[2] Pro-fragrance according to Example 10.
[3] Pro-fragrance according to Example 1.

What is claimed is:
1. A liquid laundry detergent composition comprising:
    a) from about 0.01% by weight, of a β-ketoester 3,7-dimethyl-1,6-octen-3-yl 1-(β-naphthyl)-3-oxo-propionate, 2,6-dimethyl-7-octen-2-yl 3-(4-methoxyphenyl)-3-oxo-propionate, 2,6-dimethyl-7-octen-2-yl 3-(4-nitrophenyl)-3-oxo-propionate, 2,6-dimethyl-7-octen-2-yl 3-(β-naphthyl)-3-oxo-propionate, 3,7-dimethyl-1,6-octadien-3-yl 3-(4-methoxyphenyl)-3-oxo-propionate, (α,α,-4-trimethyl-3-cyclohexenyl)methyl 3-(β-naphthyl)-3-oxo-propionate, 3,7-dimethyl-1,6-octadien-3-yl 3-(α-naphthyl)-3-oxo-propionate, cis 3-hexen-1-yl 3-(β-naphthyl)-3-oxo-propionate, 9-decen-1-yl 3-(β-naphthyl)-3-oxo-propionate, 3,7-dimethyl-1,6-octadien-3-yl 3-(nonanyl)-3-oxo-propionate, 2,6-dimethyl-7-octen-2-yl 3-(nonanyl)-3-oxo-propionate, 2,6-dimethyl-7-octen-2-yl 3-oxo-butyrate, 3,7-dimethyl-1,6-octadien-3-yl 3-oxo-butyrate, 2,6-dimethyl-7-octen-2-yl 3-(β-naphyhyl)-3-oxo-2-methylpropionate, 3,7-dimethyl-1,6-octadien- 3-yl 3-(β-naphyhyl)-3-oxo-2,2-dimethylpropionate, 3,7-dimethyl-1,6-octadien-3-yl 3-(β-naphthyl)-3-oxo-2-methylpropionate, 3,7-dimethyl-2,6-octadienyl 3-(β- naphthyl)-3-oxo-propionate, 3,7-dimethyl-2,6-octadienyl 3-heptyl-3-oxo-propionate, and mixtures thereof;

b) from about 0.01% by weight, of a detersive surfactant selected from the group consisting of anionic, cationic, nonionic, zwitterionic, ampholytic surfactants, and mixtures thereof, and c) the balance carriers;

wherein said laundry composition has a pH of from about 7.2 to about 8.9 when measured as a 10% solution in water.

2. A composition according to claim 1 comprising from about 0.01% to about 15% by weight of a β-ketoester.

3. A composition according to claim 2 comprising from about 1% to about 5% by weight of a β-ketoester.

4. A composition according to claim 3 comprising from about 0.1% to about 1% by weight of a β-ketoester.

5. A composition according to claim 1 wherein $R^1$ has the formula:

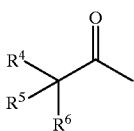

$R^2$, $R^3$, $R^4$ and $R^5$ are each hydrogen; and $R^6$ is hydrogen, $C_1$–$C_{16}$ substituted or unsubstituted linear alkyl, $C_3$–$C_{16}$ substituted or unsubstituted branched alkyl, and mixtures thereof.

6. A composition according to claim 1 comprising from about 0.1% to about 60% by weight, of a surfactant.

7. A composition according to claim 6 comprising from about 0.1% to about 30% by weight, of a surfactant.

8. A composition according to claim 1 wherein the adjunct ingredients are selected from the group consisting of dispersents, enzymes, dyes, perfumes, colorants, filler salts, hydrotropes, fluorescers, fabric conditioners, lanolin, hydrolyzable surfactants, preservatives, anti-oxidants, chelants, stabilizers, anti-shrinkage agents, germicides, fingicides, anti corrosion agents, pharmaceutical actives, and mixtures thereof.

9. A composition according to claim 1 further comprising at least about 0.001% of a protease enzyme wherein said protease enzyme is selected from the group consisting of Protease A derived from *Bacillus amyloliquefaciens*, Protease B derived from *Bacillus amyloliquefaciens*, Protease D derived from *Bacillus amyloliquefaciens*, subtilisin 309 variants derived from *Bacillus lentus*, and mixtures thereof.

10. A composition according to claim 1 wherein the adjunct ingredients are selected from the group consisting of builders, optical brighteners, bleaches, bleach boosters, bleach catalysts, bleach activators, soil release polymers, dye transfer agents, dispersents, enzymes, suds suppressers, dyes, perfumes, colorants, filler salts, hydrotropes, enzymes, photoactivators, fluorescers, fabric conditioners, hydrolyzable surfactants, preservatives, anti-oxidants, chelants, stabilizers, anti-shrinkage agents, anti-wrinkle agents, germicides, fungicides, anti corrosion agents, and mixtures thereof.

11. A non-aqueous liquid detergent composition comprising:

a) from about 49% to about 99.95% by weight, a structured, surfactant-containing liquid phase, said phase fomed by combining:

i) from about 1% to about 80% by weight of said liquid phase, one or more non-aqueous organic diluents: and ii) from about 20% to about 99% by weight of said liquid phase, a surfactant selected from the group consisting of anionic, nonionic, cationic surfactants, and mixtures thereof, b) from about 0.01% by weight, of a β-ketoester having the formula:

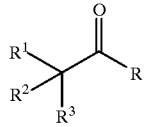

wherein R is alkoxy derived from a fragrance raw material alcohol; $R^1$ and $R^2$ are each hydrogen, $R^3$ has the formula:

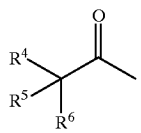

wherein $R^4$, $R^5$, and $R^6$ are taken together to form $C_6$–$C_{30}$ substituted or unsubstituted aryl; and c) the balance adjunct ingredients which are substantially insoluble in said liquid phase, said adjuncts comprising particulate material having a size from about 0.1 micron to about 1500 microns, wherein said ingredients are preferably selected from the group consisting of peroxygen bleaching agents, bleach activators, organic detergent builders, sources of alkalinity, and mixtures thereof.

12. A composition according to claim 11 comprising from about 55% to about 98.9% by weight, a structured, surfactant-containing liquid phase.

13. A composition according to claim 11 comprising from about 0.01% to about 15% by weight of a β-ketoester.

14. A composition according to claim 11 comprising from about 1% to about 5% by weight of a β-ketoester.

15. A composition according to claim 13 comprising from about 0.1% to about 1% by weight of a β-ketoester.

16. A composition according to claim 11 wherein $R^4$, $R^5$ and $R^6$ are taken together to form $C_6$–$C_{30}$ substituted or unsubstituted phenyl, naphthyl, and mixtures thereof.

17. A method for providing enduring fragrance benefits to fabric comprising the step of contacting fabric with a laundry detergent composition comprising:

a) from about 0.01% by weight, of a β-ketoester having the formula:

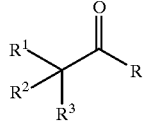

wherein R is alkoxy derived from a fragrance raw material alcohol; $R^1$, $R^2$, and $R^3$ are each independently hydrogen, $C_1$–$C_{30}$ substituted or unsubstituted linear alkyl, $C_3$–$C_{30}$ substituted or unsubstituted branched alkyl, $C_3$–$C_{30}$ substituted or unsubstituted cyclic alkyl, $C_2$–$C_{30}$ substituted or unsubstituted linear alkenyl, $C_3$–$C_{30}$ substituted or unsubstituted branched alkenyl, $C_3$–$C_{30}$ substituted or unsubstituted cyclic alkenyl, $C_2$–$C_{30}$ substituted or unsubstituted linear alkynyl, $C_3$–$C_{30}$ substituted or unsubstituted branched alkynyl, $C_6$–$C_{30}$ substituted or unsubstituted alkylenearyl, $C_6$–$C_{30}$ substituted or unsubstituted aryl, $C_2$–$C_{20}$ substituted or unsubstituted alkyleneoxy, $C_3$–$C_{20}$ substituted or unsubstituted alkyleneoxyalkyl, $C_7$–$C_{20}$ substituted or unsubstituted alkylenearyl, $C_6$–$C_{20}$ substituted or unsubstituted alkyleneoxyaryl, and mixtures thereof; provided at least one $R^1$, $R^2$, or $R^3$ is a unit having the formula:

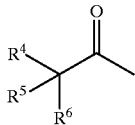

wherein $R^4$, $R^5$, and $R^6$ are each independently hydrogen, $C_1$–$C_{30}$ substituted or unsubstituted linear alkyl, $C_3$–$C_{30}$ substituted or unsubstituted branched alkyl, $C_3$–$C_{30}$ substituted or unsubstituted cyclic alkyl, $C_1$–$C_{30}$ substituted or unsubstituted linear alkoxy, $C_3$–$C_{30}$ substituted or unsubstituted branched alkoxy, $C_3$–$C_{30}$ substituted or unsubstituted cyclic alkoxy, $C_2$–$C_{30}$ substituted or unsubstituted linear alkenyl, $C_3$–$C_{30}$ substituted or unsubstituted branched alkenyl, $C_3$–$C_{30}$ substituted or unsubstituted cyclic alkenyl, $C_2$–$C_{30}$ substituted or unsubstituted linear alkynyl, $C_3$–$C_{30}$ substituted or unsubstituted branched alkynyl, $C_6$–$C_{30}$ substituted or unsubstituted alkylenearyl; or $R^4$, $R^5$, and $R^6$ can be taken together to form $C_6$–$C_{30}$ substituted or unsubstituted aryl; and mixtures thereof;

b) at least about 0.01% by weight, of a detersive surfactant selected from the group consisting of anionic, cationic, non ionic, zwitterionic, ampholytic surfactants, and mixtures thereof; and c) the balance carriers;

wherein said laundry composition has a pH of from about 7.2 to about 8.9 when measured as a 10% solution in water.

* * * * *